(12) United States Patent
Thomas et al.

(10) Patent No.: US 6,528,809 B1
(45) Date of Patent: *Mar. 4, 2003

(54) METHODS AND APPARATUS FOR TAILORING SPECTROSCOPIC CALIBRATION MODELS

(75) Inventors: Edward V. Thomas, Albuquerque, NM (US); Robert K. Rowe, Corrales, NM (US)

(73) Assignees: Rio Grande Medical Technologies, Inc., Albuquerque, NM (US); Sandia Corporation, Albuquerque, NM (US)

( * ) Notice: Subject to any disclaimer, the term of this patent is extended or adjusted under 35 U.S.C. 154(b) by 79 days.

This patent is subject to a terminal disclaimer.

(21) Appl. No.: 09/672,326

(22) Filed: Sep. 28, 2000

Related U.S. Application Data

(63) Continuation of application No. 09/415,432, filed on Oct. 8, 1999, now Pat. No. 6,157,041, which is a continuation-in-part of application No. 09/170,022, filed on Oct. 13, 1998, now abandoned.

(51) Int. Cl.[7] ............................................. G01N 15/06
(52) U.S. Cl. ............... 250/573; 250/559.1; 250/339.09
(58) Field of Search .......................... 250/573, 559.1, 250/339.09, 339.08, 339.07, 339.12; 356/346, 303, 436, 432; 364/498, 572, 413.01–413.09; 128/633–665

(56) References Cited

U.S. PATENT DOCUMENTS

| | | | |
|---|---|---|---|
| 3,508,830 A | 4/1970 | Hopkins et al. | ............ 356/103 |
| 3,769,974 A | 11/1973 | Smart et al. | ............ 128/2.05 P |
| 4,169,807 A | 10/1979 | Zuber | ........................ 252/171 |
| 4,427,889 A | 1/1984 | Muller | ........................ 250/339 |
| 4,653,880 A | 3/1987 | Sting et al. | ................ 350/620 |
| 4,655,225 A | 4/1987 | Dahne et al. | ............... 128/633 |
| 4,661,706 A | 4/1987 | Messerschmidt et al. | ... 250/341 |
| 4,712,912 A | 12/1987 | Messerschmidt | ............ 356/73 |
| 4,730,882 A | 3/1988 | Messerschmidt | ........... 350/96.1 |
| 4,852,955 A | 8/1989 | Doyle et al. | ................. 350/1.2 |
| 4,853,542 A | 8/1989 | Milosevic et al. | .......... 250/353 |
| 4,859,064 A | 8/1989 | Messerschmidt et al. | ... 356/446 |
| 4,866,644 A | 9/1989 | Shenk et al. | ........... 364/571.02 |
| 4,882,492 A | 11/1989 | Schlager | ..................... 250/346 |
| 4,975,581 A | 12/1990 | Robinson et al. | .......... 250/339 |

(List continued on next page.)

FOREIGN PATENT DOCUMENTS

| | | |
|---|---|---|
| EP | 0 280 418 A1 | 8/1988 |
| WO | WO 92/17765 | 10/1992 |
| WO | WO 93/07801 | 4/1993 |
| WO | WO 96/32631 | 10/1996 |

OTHER PUBLICATIONS

Anderson, C.E. et al., "Fundamentals of calibration Transfer Through Procrustes Analysis," *Appln. Spectros.*, vol. 53, No. 10 (1999) p. 1268. (Month unknown).

Bantle, John P. et al., "Glucose Measurement in Patients with Diabetes Mellitus with Dermal Interstitial Fluid," Copyright ©1997 by Mosby–Year Book, Inc., 9 pages. (Month unknown).

(List continued on next page.)

*Primary Examiner*—Que T. Le
(74) *Attorney, Agent, or Firm*—Crompton, Seager & Tufte, LLC

(57) ABSTRACT

A method and apparatus for non-invasively measuring a biological attribute, such as the concentration of an analyte, particularly a blood analyte in tissue such as glucose. The method utilizes spectrographic techniques in conjunction with an improved subject-tailored calibration model. In a calibration phase, calibration model data is modified to reduce or eliminate subject-specific attributes, resulting in a calibration data set modeling within- subject physiological variation, sample location, insertion variations, and instrument variation. In a prediction phase, the prediction process is tailored for each target subject separately using a minimal number of spectral measurements from each subject.

15 Claims, 14 Drawing Sheets

U.S. PATENT DOCUMENTS

| | | | |
|---|---|---|---|
| 5,015,100 A | 5/1991 | Doyle | 356/445 |
| 5,019,715 A | 5/1991 | Sting et al. | 250/571 |
| 5,028,787 A | 7/1991 | Rosenthal et al. | 250/341 |
| 5,051,602 A | 9/1991 | Sting et al. | 250/571 |
| 5,068,536 A | 11/1991 | Rosenthal | 250/341 |
| 5,070,874 A | 12/1991 | Barnes et al. | 128/633 |
| 5,158,082 A | 10/1992 | Jones | 128/633 |
| 5,179,951 A | 1/1993 | Knudson | 128/633 |
| 5,204,532 A | 4/1993 | Rosenthal | 250/341 |
| 5,222,496 A | 6/1993 | Clarke et al. | 128/633 |
| 5,224,478 A | 7/1993 | Sakai et al. | 128/633 |
| 5,225,678 A | 7/1993 | Messerschmidt | 250/339 |
| 5,230,702 A | 7/1993 | Lindsay et al. | 604/4 |
| 5,237,178 A | 8/1993 | Rosenthal et al. | 250/341 |
| 5,243,546 A | 9/1993 | Maggard | 364/571.02 |
| 5,299,570 A | 4/1994 | Hatschek | 128/633 |
| 5,311,021 A | 5/1994 | Messerschmidt | 250/339.01 |
| 5,321,265 A | 6/1994 | Block | 250/343 |
| 5,331,958 A | 7/1994 | Oppenheimer | 128/633 |
| 5,348,003 A | 9/1994 | Caro | 128/633 |
| 5,351,686 A | 10/1994 | Steuer et al. | 128/633 |
| 5,355,880 A | 10/1994 | Thomas et al. | 128/633 |
| 5,366,903 A | 11/1994 | Lundsgaard et al. | 436/165 |
| 5,372,135 A | 12/1994 | Mendelson et al. | 128/633 |
| 5,379,764 A | 1/1995 | Barnes et al. | 128/633 |
| 5,402,778 A | 4/1995 | Chance | 128/633 |
| 5,405,315 A | 4/1995 | Khuri et al. | 604/4 |
| 5,435,309 A | 7/1995 | Thomas et al. | 128/633 |
| 5,452,723 A | 9/1995 | Wu et al. | 128/664 |
| 5,459,317 A | 10/1995 | Small et al. | 250/341.1 |
| 5,459,677 A | 10/1995 | Kowalski et al. | 364/571.02 |
| 5,490,506 A | 2/1996 | Takatani et al. | 128/633 |
| 5,494,032 A | 2/1996 | Robinson et al. | 128/633 |
| 5,505,726 A | 4/1996 | Meserol | 606/9 |
| 5,507,723 A | 4/1996 | Keshaviah | 604/5 |
| 5,518,623 A | 5/1996 | Keshaviah et al. | 210/646 |
| 5,533,509 A | 7/1996 | Koashi et al. | 128/633 |
| 5,552,997 A | 9/1996 | Massart | 364/571.01 |
| 5,595,903 A * | 1/1997 | Soreq et al. | 435/240.2 |
| 5,596,992 A | 1/1997 | Haaland et al. | 128/664 |
| 5,630,413 A | 5/1997 | Thomas et al. | 128/633 |
| 5,636,633 A | 6/1997 | Messerschmidt et al. | 128/633 |
| 5,655,530 A | 8/1997 | Messerschmidt | 128/633 |
| 5,681,273 A | 10/1997 | Brown | 604/6 |
| 5,708,593 A | 1/1998 | Saby et al. | 364/571.04 |
| 5,724,268 A | 3/1998 | Sodickson et al. | 364/571.02 |
| 5,792,050 A | 8/1998 | Alam et al. | 600/310 |
| 5,823,951 A | 10/1998 | Messerschmidt et al. | 600/322 |
| 5,830,132 A | 11/1998 | Robinson | 600/310 |
| 5,857,462 A | 1/1999 | Thomas et al. | 128/633 |
| 5,933,792 A | 8/1999 | Andersen et al. | 702/32 |
| 5,935,062 A | 8/1999 | Messerschmidt et al. | 600/322 |
| 6,152,876 A | 11/2000 | Robinson et al. | 600/322 |
| 6,157,041 A | 12/2000 | Thomas et al. | 250/573 |

OTHER PUBLICATIONS

Blank, T.B. et al., "Transfer of Near–Infrared Multivariate Calibrations Without Standards," Anal. Chem., vol. 68 (1996) p. 2987. (Month unknown).

Bleyer et al., "The costs of Hospitalizations Due to Hemodialysis Access Management", Nephrology News & Issues, Jan. 1995, pp. 19–47.

Berkoben et al., "Vascular Access for Hemodialysis", Clinical Dialysis, published on or before Oct. 30, 1997, 20 pages.

Daugirdas et al. "Comparison of Methods to Predict the Equilibrated Kt/V (eKt/V) in the Hemo Study", National Institutes of Health, NIDDK, Bethesda, MD, Aug. 20, 1996.

Depner et al. "Clinical Measurement of Blood Flow in Hemodialysis Access Fistulae and Grafts by Ultrasound Dilution", from the Department of Nephrology, University of California, published on or before Oct. 30, 1997, 4 pages.

Haaland, David M. et al. "Reagentless Near–Infrared Determination of Glucose in Whole Blood Using Multivariate Calibration," Applied Spectroscopy, vol. 46, No. 10 (1992) pp. 1575–1578. (Month unknown).

Hakim et al., "Effects of Dose of Dialysis on Morbidity and Mortality", American Journal of Kidney Diseases, vol. 23, No. 5, May 1994, pp. 661–669.

Heise, H.M. "Non–Invasive Monitoring of Metabolites Using Near Infrared Spectroscopy: State of the Art," Horm. Metab. Res., vol. 28 (1996) pp. 527–534. (Month unknown).

Heise, H.M. et al., "Noninvasive Blood Glucose Sensors Based on Near–Infrared Spectroscopy," Artif Organs, vol. 18, No. 6 (1994) pp. 1–9. (Month unknown).

Jacobs et al., "A Disposable urea Sensor for Continuous Monitoring of Hemodialysis Efficiency", ASAIO Journal, 1993, pp. M353–M358. (Month unknown).

Jagemann, Kay–Uwe et al. "Application of Near–Infrared Spectroscopy for Non–Invasive Determination of Blood/Tissue Glucose Using Neural Networks," Zeitschrift for Physikalische Chemie, Bd.191, S. 179–190 (1995). Month unknown.

Khalil, Omar S., "Spectroscopic and Clinical Aspects of Noninvasive Glucose Measurements," Internet Article (Clinical Chemistry, 1999; 45:165–177) 24 pages. (Month unknown).

Keshaviah et al., "On–line monitoring of the delivery of the hemodialysis prescription", Pediatric Nephrology, vol. 9, 1995, pp. S2–S8. (Month unknown).

Korte, E.H. et al., "Infrared Diffuse Reflectance Accessory for Local Analysis on Bulky Samples," Applied Spectroscopy, vol. 42, No. 1, Jan. 1988, pp. 38–43.

Krivitski, "Theory and Validation of Access Flow Measurement by Dilution Technique During Hemodialysis", Kidney International, vol. 48, 1995, pp. 244–250. (Month unknown).

Lorber, Avraham et al., "Local Centering in Multivariate Calibration," Journal of Chemometrics, vol. 10 (1996) pp. 215–220. (Month unknown).

Malin, Stephen F., "Non–Invasive Measurement of Glucose by Near Infrared Diffuse Reflectance Spectroscopy," 31$^{st}$ Annual Oak Ridge Conference, Sigma Diagnostics, Inc., Apr. 23, 1999.

Marbach, "Measurement Techniques for IR Spectroscopic Blood Glucose Determination", 1993. (Month unknown).

Marbach, R. et al. "Noninvasive Blood Glucose Assay by Near–Infrared Diffuse Reflectance Spectroscopy of the Human Inner Lip," Applied Spectroscopy, vol. 47, No. 7 (1993) pp. 875–881 (Month unknown).

Marbach, R. et al. "Optical Diffuse Reflectance Accessory for Measurements of Skin Tissue by Near–Infrared Spectroscopy," Applied Optics, vol. 34, No. 4, Feb. 1, 1995, pp. 610–621.

McIntosh, Bruce C. et al. Quantitative Reflectance Spectroscopy in the Mid–IR, 16$^{th}$ Annual FACSS Conference, Oct. 1989.

Osborne, B.G. et al., "Optical Matching of Near Infrared Reflectance Monochromator Instruments for the Analysis of Ground and Whole Wheat," J. Near Infrared Spectrosc., vol. 7 (1999) p. 167. (Month unknown).

Ozdemir, d. et al., "Hybrid Calibration Models: An Alternative to Calibration Transfer," *Appl. Spectros.*, vol. 52, No. 4 (1998) p.599 (Month unknown).

Robinson, M. Ries et al., "Noninvasive Glucose Monitoring in Diabetic Patients: A Preliminary Evaluation," *Clinical Chemistry*, vol. 38, No. 9 (1992) pp. 1618–1622 (Month unknown).

Ronco et al., "On–line urea monitoring: a further step towards adequate dialysis prescription and delivery", *Int'l Journal of Artificial Organs*, vol. 18, No. 9, 1995, pp. 534–543. (Month unknown).

Service, F. John et al., Dermal Interstitial Glucose as an Indicator of Ambient Glycemia, *Diabetes Care*, vol. 20, No. 9, Sep. 1997, 9 pages.

Sherman, "Recirculation in the Hemodialysis Access", *Principles and Practice of Dialysis*, published on or before Oct. 30, 1997, 9 pages.

Sherman, "The Measurement of Dialysis Access Recirculation", *American Journal of Kidney Diseases*, vol. 22, No. 4, Oct. 1993, pp. 616–621.

Sjoblom, J. et al., "An Evaluation of Orthogonal Signal correction Applied to Calibration Transfer of Near Infrared Spectra," *Chemom & Intell Lab. Sys.*, vol. 44 (1998) p. 229 (Month unknown).

Steuer et al., "A New Optical Technique for Monitoring Hematocrit and Circulating Blood Volume: Its Application in Renal Dialysis", *Dialysis & Transplantation*, vol. 22, No. 5, May 1993, 5 pages.

Sum, S.T. et al., "Standardization of Fiber Optic Probes for Near–Infrared Multivariate Calibrations," *Appl. Spectros.*, vol. 52, No. 6 (1998) p. 869. (Month unknown).

Swierenga, H. et al., "Comparison of Two Different Approaches Toward Model Transferability in NIR Spectroscopy," *Appl. Spectros.*, vol. 52, No. 1 (1998) p. 7. (Month unknown).

Swierenga, H. et al., "Improvement of PLS Model Transferability by Robust Wavelength Selection," *Chemom & Intell Lab. Sys.Chemom & Intell Lab. Sys.*, vol. 14 (1998) p. 237. (Month unknown).

Wang, Y–D. et al., "Calibration Transfer and Measurement Stability of Near–Infrared Spectrometers," *Appl. Spectros.*, vol. 46, No. 5 (1992) p. 764 (Month unknown).

Wang, Y–D. et al., "Improvement of Multivariate Calibration Through Instrument Standardization," *Anal. Chem.*, vol. 64 (1992) p. 562. (Month unknown).

Wang, Z., "Additive Background Correction in Multivariate Instrument Standardization," *Anal. Chem.*, vol. 67 (1995) p. 2379. (Month unknown).

Ward, Kenneth J. et al., "Post–Prandial Blood Glucose Determination by Quantitative Mid–Infrared Spectroscopy," *Applied Spectroscopy*, vol. 46, No. 6 (1992) pp. 959–965. (Month unknown).

Webb, Paul, "Temperatures of Skin, Subcutaneous Tissue, Muscle and Core in Resting Men in Cold, Comfortable and Hot Conditions," *European Journal of Applied Physiology*, vol. 64 (1992) pp. 471–476. (Month unknown).

Brochure entitled "Determination of Delivered Therapy Through Measurement of Effective Clearance", Fresenius USA, Dec. 1994, 1 page.

Brochure entitled "Improve the Clinical Outcome of Every Patient", In Line Diagnostics, published on or before Oct. 30, 1997, 2 pages.

* cited by examiner

Figure 2 - Calibration via Mean Center

Figure 3 Direct Tailored Prediction

Figure 4 Composite Tailored Prediction

Figure 5 - Calibration via Fixed Reference

Figure 6 - Calibration via Round Robin $Y^L$ = Library of reference spectra
$G^L$ = Library of reference values Figure 7 - Calibration via Similar References $Y^L$ denotes the library of spectra
$G^L$ denotes the corresponding library of reference values Figure 8 Matched Spectrum & Direct Tailored Prediction Figure 9 Matched Spectrum & Composite Tailored Prediction Figure 10 – Spectrum of Generic Model Coefficients Figure 11 - Direct Tailored Generic Model Performance: Subject 1

Figure 12 - Direct Tailored Generic Model Performance: Subject 2

METHODS AND APPARATUS FOR TAILORING SPECTROSCOPIC CALIBRATION MODELS

CROSS REFERENCE TO CO-PENDING APPLICATIONS

The present continuation of pending application Ser. No. 09/415,432, filed Oct. 8, 1999, now U.S. Pat. No. 6,157,041.

TECHNICAL FIELD

The present invention relates generally to methods for multivariate calibration and prediction and their application to the non-invasive or non-destructive measurement of selected properties utilizing spectroscopy methods. A specific implementation of the invention relates to the situation where the multivariate calibration and prediction methods are utilized in a situation wherein biological tissue is irradiated with infrared energy having at least several wavelengths and differential absorption by the biological tissue sample is measured to determine an analyte concentration or other attribute of the tissue by application of the calibration model to the resulting spectral information.

BACKGROUND OF THE INVENTION

The need and demand for an accurate, non-invasive method for determining attributes of tissue, other biological samples or analyte concentrations in tissue or blood are well documented. For example, accurate non-invasive measurement of blood glucose levels in patients, particularly diabetics, would greatly improve treatment. Barnes et al. (U.S. Pat. No. 5,379,764) disclose the necessity for diabetics to frequently monitor glucose levels in their blood. It is further recognized that the more frequent the analysis, the less likely there will be large swings in glucose levels. These large swings are associated with the symptoms:and complications of the disease, whose long-tern effects can include-heart disease, arteriosclerosis, blindness, stroke, hypertension, kidney failure, and premature death. As described below, several systems have been proposed for the non-invasive measurement of glucose in blood. However, despite these efforts, a lancet cut into the finger is still necessary for all presently commercially available forms of home glucose monitoring. This is believed so compromising to the diabetic patient that the most effective use of any form of diabetic management is rarely; achieved.

The various proposed non-invasive methods for determining blood glucose level generally utilize quantitative infrared spectroscopy as a theoretical basis for analysis. In general, these methods involve probing glucose containing tissue using infrared radiation in absorption or attenuated total reflectance mode. Infrared spectroscopy measures the electromagnetic radiation (0.7–25 $\mu$m) a substance absorbs at various wavelengths. Molecules do not maintain fixed positions with respect to each other, but vibrate back and forth about an average distance. Absorption of light at the appropriate energy causes the molecules to become excited to a higher vibration level. The excitation of the molecules to an excited state occurs only at certain discrete energy levels, which are characteristic for that particular molecule. The most primary vibrational states occur in the mid-infrared frequency region (i.e., 2.5–25 $\mu$m). However, non-invasive analyte determination in blood in this region is problematic, if not impossible, due to the absorption of the light by water. The problem is overcome through the use of shorter wavelengths of light which are not as attenuated by water. Overtones of the primary vibrational states exist at shorter wavelengths and enable quantitative determinations at these wavelengths.

It is known that glucose absorbs at multiple frequencies in both the mid- and near-infrared range. There are, however, other infrared active analytes in the tissue and blood that also absorb at similar frequencies. Due to the overlapping nature of these absorption bands, no single or specific frequency can be used for reliable non-invasive glucose measurement. Analysis of spectral data for glucose measurement thus requires evaluation of many spectral intensities over a wide spectral range to achieve the sensitivity, precision, accuracy, and reliability necessary for quantitative determination. In addition to overlapping absorption bands, measurement of glucose is further complicated by the fact that glucose is a minor component by weight in blood and tissue, and that the resulting spectral data may exhibit a non-linear response due to both the properties of the substance being examined and/or inherent non-linearities in optical instrumentation.

A further common element to non-invasive glucose measuring techniques is the necessity for an optical interface between the body portion at the point of measurement and the sensor element of the analytical instrument. Generally, the sensor element must include an input element or means for irradiating the sample point with the infrared energy. The sensor element must further include an output element or means for measuring transmitted or reflected energy at various wavelengths resulting from irradiation through the input element. The optical interface also introduces variability into the non-invasive measurement.

Robinson et al. (U.S. Pat. No. 4,975,581) disclose a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as glucose, but also may be any chemical or physical property of the sample. The method of Robinson et al. involves a two-step process that includes both calibration and prediction steps. In the calibration step, the infrared light is coupled to calibration samples of known characteristic values so that there is differential attenuation of at least several wavelengths of the infrared radiation as a function of the various components and analytes comprising the sample with known characteristic value. The infrared light is coupled to the sample by passing the light through the sample or by reflecting the light from the sample. Absorption of the infrared light by the sample causes intensity variations of the light that are a function of the wavelength of the light. The resulting intensity variations at the at least several wavelengths are measured for the set of calibration samples of known characteristic values. Original or transformed intensity variations are then empirically related to the known characteristic of the calibration samples using a multivariate algorithm to obtain a multivariate calibration model. In the prediction step, the infrared light is coupled to a sample of unknown characteristic value, and the calibration model is applied to the original or transformed intensity variations of the appropriate wavelengths of light measured from this unknown sample. The result of the prediction step is the estimated value of the characteristic of the unknown sample. The disclosure of Robinson et al. is incorporated herein by reference.

Barnes et al. (U.S. Pat. No. 5,379,764) disclose a spectrographic method for analyzing glucose concentration wherein near infrared radiation is projected on a portion of the body, the radiation including a plurality of wavelengths, followed by sensing the resulting radiation emitted from the portion of the body as affected by the absorption of the body. The method disclosed includes pretreating the resulting data to minimize influences of offset and drift to obtain an expression of the magnitude of the sensed radiation as modified.

Dähne et al. (U.S. Pat. No. 4,655,225) disclose the employment of near infrared spectroscopy for non-invasively transmitting optical energy in the near infrared spectrum through a finger or earlobe of a subject. Also discussed is the use of near infrared energy diffusely reflected from deep within the tissues. Responses are derived at two different wavelengths to quantify glucose in the subject. One of the wavelengths is used to determine background absorption, while the other wavelength is used to determine glucose absorption.

Caro (U.S. Pat. No. 5,348,003) discloses the use of temporally modulated electromagnetic energy at multiple wavelengths as the irradiating light energy. The derived wavelength dependence of the optical absorption per unit path length is compared with a calibration model to derive concentrations of an analyte in the medium.

Wu et al. (U.S. Pat. No. 5,452,723) disclose a method of spectrographic analysis of a tissue sample which includes measuring the diffuse reflectance spectrum, as well as a second selected spectrum, such as fluorescence, and adjusting the spectrum with the reflectance spectrum. Wu et al. assert that this procedure reduces the sample-to-sample variability.

The intended benefit of using models such as those disclosed above, including multivariate analysis as disclosed by Robinson, is that direct measurements that are important but costly, time consuming, or difficult to obtain, may be replaced by other indirect measurements that are cheaper and easier to get. However, none of the prior art modeling methods, as disclosed, has proven to be sufficiently robust or accurate to be used as a surrogate or replacement for direct measurement of an analyte such as glucose.

Of particular importance to the present invention is the use of multivariate analysis. Measurement by multivariate analysis involves a two-step process. In the first step, calibration, a model is constructed utilizing a dataset obtained by concurrently making indirect measurements and direct measurements (e.g., by invasively drawing or taking and analyzing a biological sample such as blood for glucose levels) in a number of situations spanning a variety of physiological and instrumental conditions. A general form for the relationship between direct (blood-glucose concentration) and the indirect (optical) measurements is $\hat{G}=f(y_1, y_2, \ldots, y_q)$, where $\hat{G}$ is the desired estimated value of the direct measurement (glucose), $f$ is some function (model), and $y_1, y_2, \ldots, y_q$ (the arguments of $f$) represents the indirect (optical) measurement, or transformed optical measurements, at q wavelengths. The goal of this first step is to develop a useful function, $f$. In the second step, prediction, this function is evaluated at a measured set of indirect (optical) measurements $\{y_1, y_2, \ldots, y_q\}$ in order to obtain an estimate of the direct measurement (blood-glucose concentration) at some time in the future when optical measurements will be made without a corresponding direct or invasive measurement.

Ideally, one would prefer to develop a calibration model that is applicable across all subjects. Many such systems have been proposed as discussed above. However, it has been shown that for many applications the variability of the items being measured makes it difficult to develop such a universal calibration model. For the glucose application, the variability is across subjects with respect to the optical appearance of tissue and, possibly, across the analyte within the tissue.

FIG. 1 indicates the levels of spectral variation observed both among and within subjects during an experiment in which 84 measurements were obtained from each of 8 subjects. Sources of spectral variation within a subject include: spatial effects across the tissue, physiological changes within the tissue during the course of the experiment, sampling effects related to the interaction between the instrument and the tissue, and instrumental/environmental effects. The spectral variation across subjects is substantially larger than the sum of all effects w within a subject. In this case the subjects were from a relatively homogeneous population. In the broader population it is expected that spectral variation across subjects will be substantially increased. Thus, the task of building a universal calibration model is a daunting one.

In order to avoid the issue of variability across subjects, one approach involves building a completely new model for each subject. Such a method involves a substantial period of observation for each subject, as taught by R. Marbach et al., "Noninvasive Blood Glucose Assay by Near-Infrared Diffuse Reflectance Spectroscopy of the Human Inner Lip," *Applied Spectroscopy*, 1993, 47, 875–881. This method would be inefficient and impractical for commercial glucose applications due to the intensive optical sampling that would be needed for each subject.

Another approach taught by K. Ward et al., "Post-Prandial Blood Glucose Determination by Quantitative Mid-Infrared Spectroscopy," *Applied Spectroscopy*, 1992, 46, 959–965, utilizes partial least-squares multivariate calibration models based on whole blood glucose levels. When the models were based on in vitro measurements using whole blood, a subject-dependent concentration bias was retrospectively observed, indicating that additional calibration would be necessary.

In an article by Haaland et al., "Reagentless Near-Infrared Determination of Glucose in Whole Blood Using Multivariate Calibration," *Applied Spectroscopy*, 1992, 46, 1575–1578, the authors suggest the use of derivative spectra for reducing subject-to-subject (or inter-subject) spectral differences. The method was not found to be effective on the data presented in the paper. First derivatives are an example of a general set of processing methods that are commonly used for spectral pretreatment. A general but incomplete list of these pretreatment methods would include trimming, wavelength selection, centering, scaling, normalization, taking first or higher derivatives, smoothing, Fourier transforming, principle component selection, linearization, and transformation. This general class of processing methods has been examined by the inventors and has not been found to effectively reduce the spectral variance to the level desired for clinical prediction results.

In an article by Lorber et al., "Local Centering in Multivariate Calibration," *Journal of Chernometrics*, 1996, 10, 215–220, a method of local centering the calibration data by using a single spectrum is described. For each unknown sample, the spectrum used for centering the calibration data set is selected to be that spectrum that is the closest match (with respect to Mahalanobis distance) to the spectrum of the unknown. A separate partial least-squares model is then constructed for each unknown. The method does not reduce the overall spectroscopic variation in the calibration data set.

Accordingly, the need exists for a method and apparatus for non-invasively measuring attributes of biological tissue, such as glucose concentrations in blood, which incorporates a model that is sufficiently robust to act as an accurate surrogate for direct measurement. The model would preferably account for variability both between subjects and within the subject on which the indirect measurement is being used as a predictor. In order to be commercially successful, applicants believe, the model should not require extensive sampling of the specific subject on which the model is to be applied in order to accurately predict a biological attribute such as glucose. Extensive calibration of each subject is currently being proposed by BioControl Inc. In a recent press release the company defines a 60-day calibration procedure followed by a 30-day evaluation period.

The present invention addresses these needs as well as other problems associated with existing models and calibrations used in methods for non-invasively measuring an attribute of a biological sample such as glucose concentration in blood. The present invention also offers further advantages over the prior art and solves problems associated therewith.

SUMMARY OF THE INVENTION

The present invention is a method that reduces the level of interfering spectral variation that a multivariate calibration model needs to compensate for. An important application of the invention is the non-invasive measurement of an attribute of a biological sample such as an analyte, particularly glucose, in human tissue. The invention utilizes spectroscopic techniques in conjunction with improved protocols and methods for acquiring and processing spectral data. The essence of the invention consists of protocols and data-analytic methods that enable a clear definition of intra-subject spectral effects while reducing inter-subject spectral effects. The resulting data, which have reduced inter-subject spectroscopic variation, can be utilized in a prediction method that is specific for a given subject or tailored (or-adapted) for use on the specific subject. The prediction method uses a minimal set of reference samples from that subject for generation of valid prediction results.

A preferred method for non-invasively measuring a tissue attribute, such as the concentration of glucose in blood, includes first providing an apparatus for measuring infrared absorption by a biological sample such as an analyte containing tissue. The apparatus preferably includes generally three elements, an energy source, a sensor element, and a spectrum analyzer. The sensor element includes an input element and an output element. The input element is operatively connected to the energy source by a first means for transmitting infrared energy. The output element is operatively connected to the spectrum analyzer by a second means for transmitting infrared energy.

In practicing a preferred method of the present invention, an analyte containing tissue area is selected as the point of analysis. This area can include the skin surface on the finger, earlobe, forearm, or any other skin surface. A preferred sample location is the underside of the forearm. The sensor element, which includes the input element and the output element, is then placed in contact with the skin. In this way, the input element and output element are coupled to the analyte containing tissue or skin surface In analyzing for a biological attribute, such as the concentration of glucose in the analyte containing tissue, light energy from the energy source is transmitted via a first means for transmitting infrared energy into the input element. The light energy is transmitted from the input element to the skin surface. Some of the light energy contacting the analyte-containing sample is differentially absorbed by the various components and analytes contained therein at various depths within the sample. A quantity of light energy is reflected back to the output element. The non-absorbed reflected light energy is then transmitted via the second means for transmitting infrared energy to the spectrum analyzer. As detailed below, the spectrum analyzer preferably utilizes a computer and associated memory to generate a prediction result utilizing the measured intensities and a calibration model from which a multivariate algorithm is derived.

The viability of the present invention to act as an accurate and robust surrogate for direct measurement of biological attributes in a sample such as glucose in tissue, resides in the ability to generate accurate predictions of the direct measurement (e.g., glucose level) via the indirect measurements (spectra). Applicants have found that, in the case of the noninvasive prediction of glucose by spectroscopic means, application of known multivariate techniques to spectral data, will not produce a predictive model that yields sufficiently accurate predictions for future use. In order to obtain-useful predictions, the spectral contribution from the particular analyte or attribute of interest must be extracted from a complex and varying background of interfering signals. The interfering signals vary across and within subjects and can be broadly partitioned into "intra-subject" and "inter-subject" sources. Some of these interfering signals arise from other substances that vary in concentration. The net effect of the cumulative interfering signals is such that the application of known multivariate analysis methods does not generate prediction results with an accuracy that satisfies clinical needs.

The present invention involves a prediction process that reduces the impact of subject-specific effects on prediction through a tailoring process, while concurrently facilitating the modeling of intra-subject effects. The tailoring process is used to adapt the model so that it predicts accurately for a given subject. An essential experimental observation is that intra-subject spectral effects are consistent across subjects. Thus, intra-subject spectral variation observed from a set of subjects can be used to enhance or strengthen the calibration for subsequent use on an individual not included in the set. This results in a prediction process that is specific for use on a given subject, but where intra-subject information from other subjects is used to enhance the performance of the monitoring device.

Spectroscopic data that have been acquired and processed in a manner that reduces inter-subject spectroscopic variation while maintaining intra-subject variation are herein referred to as generic calibration data. These generic data, which comprise a library of intra-subject variation, are representative of the likely variation that might be observed over time for any particular subject. In order to be effective, the intra-subject spectral variation manifested in the generic calibration data must be representative of future intra-subject spectral effects such as those effects due to physiological variation, changes in the instrument status, sampling techniques, and spectroscopic effects associated with the analyte of interest. Thus, it is important to use an appropriate experimental protocol to provide representation of these intra-subject spectral effects.

In each prediction embodiment of the present invention, multivariate techniques are applied to the generic calibration data to derive a subject-specific predictor of the direct measurement. Each prediction embodiment uses the generic calibration data in some raw or altered condition in conjunction with at most a few reference spectra from a specific subject to achieve a tailored prediction method that is an accurate predictor of a desired indirect measurement for that particular subject. Reference spectra are spectroscopic measurements from a specific subject that are used in the development of a tailored prediction model. Reference analyte values quantify the concentration of the analyte (via direct methods) and can be used in the development of a tailored prediction model. Applicants have developed several embodiments that incorporate the above concepts.

Each tailored prediction method described herein utilizes generic calibration data. Generic calibration data can be created by a variety of data acquisition and processing methods. In a first preferred processing method, the generic calibration data are obtained by acquiring a series of indirect measurements from one or more subjects and a direct measurement for each subject corresponding to each indirect measurement. An appropriate experimental protocol is needed to provide adequate representation of intra-subject effects that are expected in the future (including those associated with the analyte of interest). The mean indirect measurement and the mean direct measurement for each subject based on the number of measurements from that subject are then formed. The indirect measurements are mean centered by subtracting the mean indirect measurement of each subject from each of that subject's indirect measurements. The direct measurements are mean centered by subtracting the mean direct measurement of each subject from each of that subject's direct measurements. That is, the subject-specific mean indirect measurements and subject-specific mean direct measurements act as subject-specific subtrahends. The sets of mean-centered measurements (indirect and direct) comprise the generic calibration data.

There are a number of other related ways for creating generic calibration data with a subject-specific subtrahend. For example, the subject-specific subtrahends for the indirect and direct measurements could be some linear combination of each subject's indirect and direct measurements, respectively.

In one other specific method for creating generic calibration data, the subject-specific subtrahends for the indirect and direct measurements consist of the mean of the first S indirect measurements of each subject and the mean of the first S direct measurements of each subject, respectively. Alternately, a moving window reference technique could be utilized wherein the subtrahends are the subject-specific means of the S nearest (in time) indirect and direct measurements, where S is less than the total number of reference measurements made on a particular subject. The value of S can be chosen to fit the constraints of the particular application, neglecting effects due to random noise and reference error.

In another alternative processing, method, the generic calibration data can be produced in a round-robin reference manner wherein you subtract each of the patient's reference data from every other reference measurement made on that subject in a round-robin fashion.

In a further alternative processing method which is particularly useful when a spectral library associated with a large number of subjects exists, the generic calibration data are created by subtracting some linear combination of spectral library data in order to minimize inter-subject spectral features. Subject-specific attributes can be reduced by subtracting some linear combination of similar spectra. That is, the subject-specific subtrahend for a given subject consists of a linear combination of spectra obtained from one or more subjects each of whom are different than the given subject. In one embodiment, the spectrum of a given subject would be matched with a combination of similarly appearing spectra from other subjects. In another embodiment, one would match the spectrum of a given subject with a combination of spectra from other subjects where the matching criteria involve measurable parameters such as age, gender, skin thickness, etc.

In a final alternative processing method, the generic calibration data are created through simulation in a manner that minimizes subject-specific spectral attributes. This methodology requires accurate simulations of patient spectra, as well as accurate modeling of the optical system, the sampler-tissue interface, and the tissue optical properties which all contribute to such spectral variation. Generic calibration data can be simulated directly or subject data can be simulated. The simulated subject spectra can subsequently be processed by any of the preceding five processing methods. In an additional embodiment, the simulated data can be combined with real patient data for the creation of a hybrid generic calibration data.

Once the generic calibration data have been created, such data is then utilized to create a tailored prediction process specific for a particular subject for use in future predictions of the biological attribute. The tailored prediction process can be accomplished in several ways.

The most straightforward and direct way to tailor the prediction process to a given subject is as follows and will be denoted as direct tailoring. First, the generic calibration data are used to develop an intra-subject calibration model for the analyte of interest. This model herein is referred to as a generic model. By design, the generic model will produce predictions that are essentially unaffected by intra-subject spectral variation that is represented in the generic calibration data and not associated with the analyte of interest. On the other hand, the generic model will produce predictions that are appropriately sensitive to the analyte of interest. The generic model is applied directly to at least one indirect measurement from a target subject for whom there are corresponding direct measurements. The resulting predictions of the generic model are averaged. The difference between the average of the direct measurements and average prediction is computed. This subject-specific difference is added to the subsequent predictions of the generic model as applied directly to the future indirect measurements from the target subject. The resultant sums comprise the net predictions of the direct measurement corresponding to the future indirect measurements from the target subject. It is important to note that a single generic model can be used in the tailoring process for a number of target subjects.

A second tailored prediction embodiment uses a combination of at least two subject reference spectra, reference analyte values and the generic calibration data to create a prediction model that is specific for use on the particular subject. The technique by which the calibration data and reference spectra are combined uses a linear combination of the data in absorbance units. The combinations of calibration data and reference data can be done in a structured or random way. It is the applicant's observation that random associations work effectively and are easily implemented, The process of creating these composite data is referred to as robustification. The resulting calibration spectra contain the reference spectra from the particular patient combined with spectral data that contains sources of spectroscopic variation associated with physiological variations, variations associated with sampling techniques, instrument variation and spectroscopic effects associated with the analyte of interest. The composite calibration data can be processed to develop a calibration model. The resulting model will be referred to hereafter as a composite calibration model. The resulting composite calibration model is specific for a particular patient and can be used to generate analyte prediction results for the particular subject.

In the use of either tailored prediction process, reference spectra and reference analyte values are utilized. The reference information is used in combination with the generic calibration data to create a tailored prediction process for use on the particular subject. In general terms the subject reference information is used to tailor a general processing method for use on a particular subject. In an additional embodiment, the subject reference spectra can be replaced by the use of a subject-matched spectrum or a set of matched spectra. Matched spectra are spectra from another subject or a combined spectrum that interacts with the calibration model in a manner similar to the subject to be predicted upon. In use, a never-before-seen subject is tested and at least one spectrum is obtained. The resulting spectrum is used for generating a prediction result and as a reference spectrum. In use and in contrast to the two prior embodiments no reference analyte value is used or needed. The implementation of this method requires the following:

1. Identification or creation of a matched spectra through use of the reference spectra.
2. Replacement of the reference spectra with the corresponding matched spectra.
3. Although reference analyte values are not obtained from the never-before-seen patient, matched analyte values from the corresponding matched spectra are used in the processing method in a manner consistent with the prior uses of reference analyte values.
4. Use of either tailored prediction process.

In practice, the spectral data from the never-before-seen subject is compared with spectral data that has corresponding biological attribute reference values in a spectral library to identify the best method or several matched spectra. Matched spectra are spectra from another subject that appear similar when processed by the calibration model. Applicants have observed that identical twins are well matched from a spectroscopic model perspective.

As stated previously, the application of known multivariate analysis techniques have not resulted in glucose prediction results at a clinically relevant level. The processing method described overcomes these known limitations by using a matched spectrum. Thus, the subject tailoring with this method is accomplished without an actual reference analyte value from the individual. The matched spectrum method in conjunction with either tailored prediction process requires a large spectral library to facilitate the appropriate matching between the subject to be predicted upon and at least one library spectrum. In implementation of this matching method, applicants have identified matched spectra by finding those spectra that are most consistent with the calibration model as reflected by such parameters as Mahalanobis distance and spectral residual metrics. Other methods of spectral match would also have applicability for determination of matched spectra.

These and various other advantages and features of novelty that characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF PREFERRED EMBODIMENTS

Figure 1:
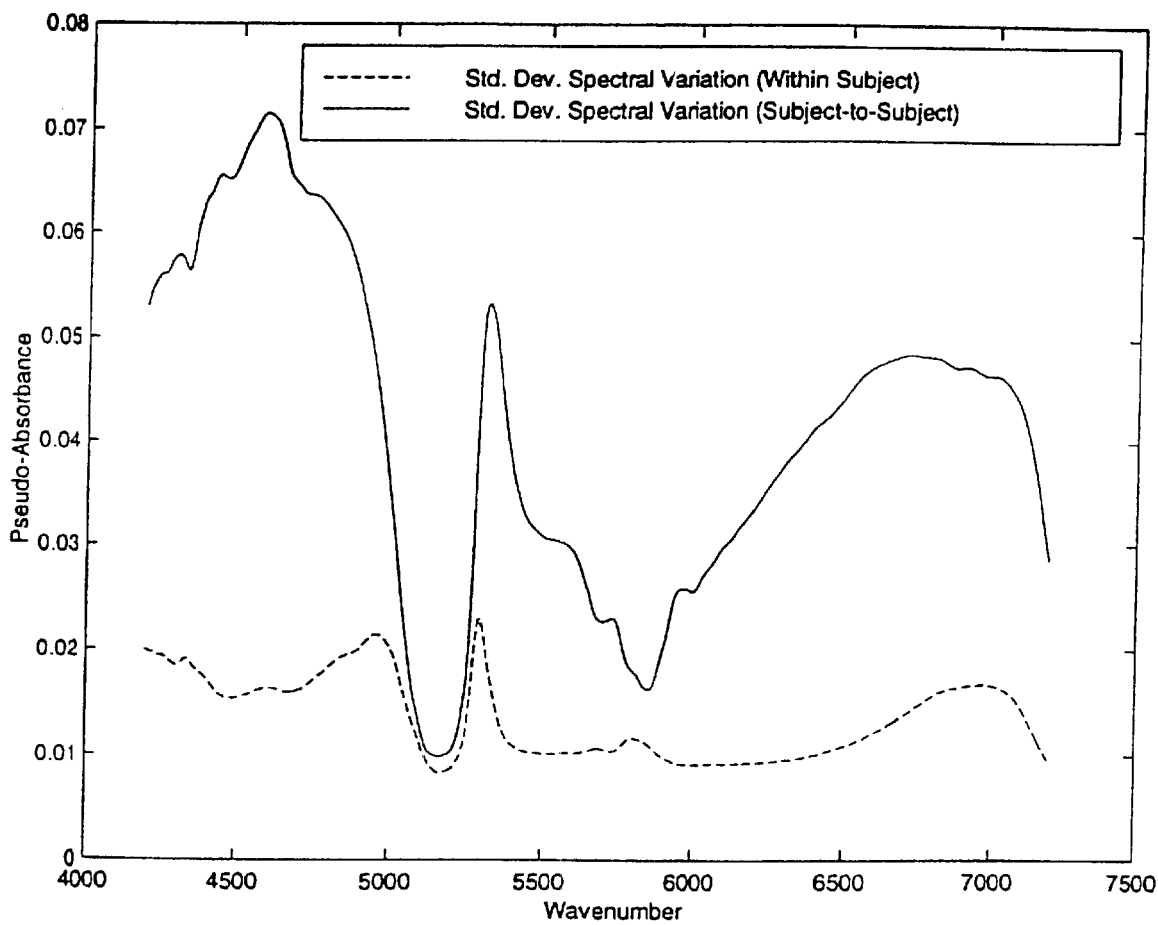
FIG. 1 depicts exemplary spectral variation observed in subjects.

Detailed descriptions of the preferred embodiments of the present invention are disclosed herein. However, it is to be understood that the disclosed embodiments are merely exemplary of the present invention that may be embodied in various systems. Therefore, specific details disclosed herein are not to be interpreted as limiting, but rather as a basis for the claims and as a representative basis for teaching one of skill in the art to variously practice the invention.

The present invention is directed to a method for non-invasive measurement of biological attributes, such as tissue analytes or properties using spectroscopy. It has been found that the sample is a complex matrix of materials with differing refractive indices and absorption properties. Further, because the tissue or blood constituents of interest are present at very low concentrations, it has been found necessary to incorporate a mathematical model derived using multivariate analysis. However, known methods of applying multivariate analysis to spectral data from a broad range of subjects have failed to produce a sufficiently accurate and robust model. To this point, these failures are largely a consequence of inadequate experimental protocols and inadequate data analytic methods. The present invention solves these deficiencies via improvements in experimental protocols and data analytic procedures. Experimental protocols have been improved in the sense that the acquisition of a wide variety of intra-subject spectral variation is emphasized. Coinciding with the improved protocols are data analytic methods that modify the calibration data to reduce subject-specific spectral attributes that are unrelated to measuring the biological attributes of interest. The resulting modified calibration data set thus facilitates the development of models that perform well in the presence of actual within-patient physiological variation. The prediction methodologies using this core concept are detailed below, subsequent to a description of the method and apparatus used for non-invasive measurement in conjunction the model.

The present invention utilizes light energy in the near-infrared region of the optical spectrum as an energy source for analysis. Water is by far the largest contributor to absorption in tissue in the near-infrared region because of its concentration, as well as its strong absorption coefficient. It has been found that the total absorption spectrum of tissue, therefore, closely resembles the water spectrum. Less than 0.1 percent of the absorption of light is from, for instance, a constituent such as glucose. It has been further found that tissue greatly scatters light because there are many refractive index discontinuities in a typical tissue sample. Water is perfused through the tissue, with a refractive index of 1.33. Cell walls and other features of tissue have refractive indices closer to 1.5 to 1.6. These refractive index discontinuities give rise to scatter. Although these refractive index. discontinuities are frequent, they are also typically small in magnitude and the scatter generally has a strong directionality toward the forward direction.

This forward scatter has been described in terms of anisotropy, which is defined as the cosine of the average scatter angle. Thus, for complete backward scatter, meaning that all scatter events would cause a photon to divert its direction of travel by 180 degrees, the anisotropy factor is −1. Likewise, for complete forward scatter, the anisotropy factor is +1. In the near infrared, tissue has been found to have an anisotropy factor of around 0.9 to 0.95, which is very forward scattering. For instance, an anisotropy factor of 0.9 means that an average photon of light only scatters through an angle of up to 25 degrees as it passes through the sample.

In analyzing for an analyte in tissue, measurements can be made in at least two different modes. It is recognized that one can measure light transmitted through a section of tissue, or one may measure light reflected or remitted from tissue. It has been recognized that transmission is the preferred method of analysis in spectroscopy because of the forward scattering of light as it passes through the tissue. However, it is difficult to find a part of the body which is optically thin enough to pass near infrared light through, especially at the longer wavelengths. Thus, the preferred method for measurement in the present invention is to focus on the reflectance of light from the sample. Preferred apparatus and methods for conducting such measurements are disclosed by Robinson in U.S. Pat. No. 5,830,132, the disclosure of which is incorporated herein by reference.

In preferred embodiments of an apparatus for non-invasively measuring a biological attribute such as a blood analyte concentration, several elements are combined in conjunction with a mathematical model. The apparatus generally includes three elements, an energy source, a sensor element, and a spectrum analyzer. The sensor element preferably includes an input element and an output element, which can include a single lens system for both input and output light energy, as for example a fiber optic bundle. The input element and output element are in contact with a common skin surface of an analyte-containing tissue. In an alternative embodiment, an alternative sensor element arrangement is used, wherein the input element and output element are arranged on opposing surfaces of an analyte containing tissue. Both embodiments function to give a measure of the absorption of infrared energy by the analyte-containing tissue. However, the first embodiment is utilized to measure the quantity of light energy that is reflected from the analyte-containing tissue by the analyte components therein. In contrast, the second embodiment measures the transmission of light energy through the analyte-containing tissue. In either embodiment, the absorption at various wavelengths can be determined by comparison to the intensity of the light energy from the energy source.

The energy source is preferably a wide band, infrared black body source. The optical wavelengths emitted from the energy source are preferably between 1.0 and 2.5 $\mu$m. The energy source is operatively coupled to a first means for transmitting infrared energy from the energy source to the input element. In preferred embodiments, this first means can simply include the transmission of light energy to the input element through air by placing the energy source proximate the input element or use of a fiber optic cable.

The input element of the sensor element is preferably an optical lens or fiber that focuses the light energy to a high energy density spot. However, it is understood that other beam focusing means may be utilized in conjunction with the optical lens to alter the area of illumination. For example, a multiple lens system, tapered fibers, or other conventional optical beam-shaping devices could be utilized to alter the input light energy.

In both embodiments, an output sensor is utilized to receive reflected or transmitted light energy from the analyte containing tissue. As described in conjunction with a method of analysis below, the first embodiment has an output sensor that receives reflected light energy, while the second-embodiment of includes an output sensor which receives transmitted light through the analyte-containing tissue. As with the input element, the output element is preferably an optical lens or fiber optic. Other optical collection means may be incorporated into an output element, such as a multiple lens system, tapered fiber, or other beam-collection means to assist in directing the light energy to the spectrum analyzer.

A second means for transmitting infrared energy is operatively connected to the output element. The light transmitted through the second means for transmitting infrared energy is transmitted to the spectrum analyzer. In a preferred embodiment, the operative connection to the output element includes transmission of the reflected or transmitted light energy exiting the output element through a fiber optic or air to the spectrum analyzer. A mirror or series of mirrors may be utilized to direct this light energy to the spectrum analyzer. In a preferred embodiment, a specular control, device is incorporated to separate the specular reflected light from diffusely reflected light. This device is disclosed in co-pending and commonly assigned application Ser. No.

08/513,094, filed Aug. 9, 1995, and entitled "Improved Diffuse Reflectance Monitoring Apparatus," now U.S. Pat. No. 5,636,633, issued Jun. 10, 1997, the disclosure of which is incorporated herein by reference.

In practicing a preferred method of the present invention, an analyte-containing tissue area is selected as the point of analysis. A preferred sample location is the underside of the forearm. The sensor element, which includes the input element and the output element, is then placed in contact with the sample area.

In analyzing for a biological attribute, such as for the concentration of glucose in the analyte-containing tissue, light energy from the energy source is transmitted through the first means for transmitting infrared energy into the input element. The light energy is transmitted from the input element to the skin surface. The light energy contacting the skin surface is differentially absorbed by the various components and analytes contained below the skin surface within the body (i.e., blood within vessels) therein. In a preferred embodiment, the non-absorbed light energy is reflected back to the output element. The non-absorbed light energy is transmitted via the second means for transmitting infrared energy to the spectrum analyzer.

In a preferred embodiment, a biological attribute, such as the concentration of glucose in the tissue, is determined by first measuring the light intensity received by the output sensor. These measured intensities in combination with a calibration model are utilized by a multivariate algorithm to predict the glucose concentration in the tissue. In preferred embodiments, the calibration model empirically relates the known biological attribute in the calibration samples to the measured intensity variations obtained from the calibration samples. The spectrum analyzer of the present invention preferably includes a frequency dispersion device and photodiode array detectors in conjunction with a computer to apply the data received from such devices to the model stored therein to predict the biological attribute of interest of the subject.

As previously stated, the computer includes a memory having stored therein a multivariate calibration model empirically relating known biological attributes, such as glucose concentration, in a set of calibration samples to the measured intensity variations from the calibration samples, at several wavelengths. The present invention includes prediction methodologies with sufficient accuracy to act as a surrogate predictor of biological attributes so that direct measurements can be dramatically reduced or eliminated.

Generally, the method of the present invention incorporates generic calibration data in combination with subject-specific data to create a tailored prediction process. The resulting subject-tailored prediction process combines selected portions of multiple subject spectral variances and subject reference spectra. The tailored prediction process is made subject specific by incorporating a minor amount of subject-specific spectral data and does not require extensive calibration testing of the individual subject on which the model is to be applied. The various embodiments described below require data collection and processing to be applied in both a calibration and a prediction phase.

In the calibration phase, the methods generally require the realization of calibration data that has been modified in such a way as to reduce or eliminate subject-specific spectral attributes that are unrelated to the biological attribute of interest in the test. The resulting modified calibration data has reduced inter-subject spectroscopic variation while maintaining other relevant sources of spectroscopic variation. Other known sources of spectroscopic variation include within subject physiological variation, variation associated with sampling errors, instrument variation, and spectroscopic effects associated with the analyte or attribute of interest. Such calibration data is referred to herein as generic calibration data.

In the prediction phase, two general embodiments are incorporated. The first method focuses on developing a model from the generic calibration data followed by introducing subject-specific data from a particular individual, whose attributes are to be predicted, and utilizing this information to create a subject specific prediction through use of the generic model. The second general approach includes incorporating subject-specific data from an individual subject to be tested along with the generic calibration data. The resulting composite data is used in the multivariate analysis to generate a prediction function. The resulting prediction function resulting from the combination of generic calibration data and subject-specific data is a composite calibration model that is subject specific.

In all embodiments, a model is developed using spectroscopic variation from multiple subjects wherein the tailored prediction method uses one or more reference spectroscopic measurements from a specific patient so that the prediction process becomes subject tailored for that specific subject. Applicants have found that the model is an accurate predictor because it incorporates the physiological variation from other subjects to enhance or strengthen a calibration for subsequent use on a given individual. The prediction procedure results in a method that is specific for use on a given subject, but where information not from the subject is used to enhance prediction accuracy, in combination with spectral information from that particular individual.

In practicing the present invention, the first step of one preferred method is to generate generic calibration data that is essentially free from subject-specific effects. This step may be accomplished by utilizing a device such as disclosed in the aforementioned Robinson U.S. Pat. No. 4,975,581 to indirectly measure from one to many subjects, each at a variety of physiological (such as taking glucose measurement over a period of time) and spatial (such as taking glucose measurements from a variety of locations on the body) states.

Figure 2:
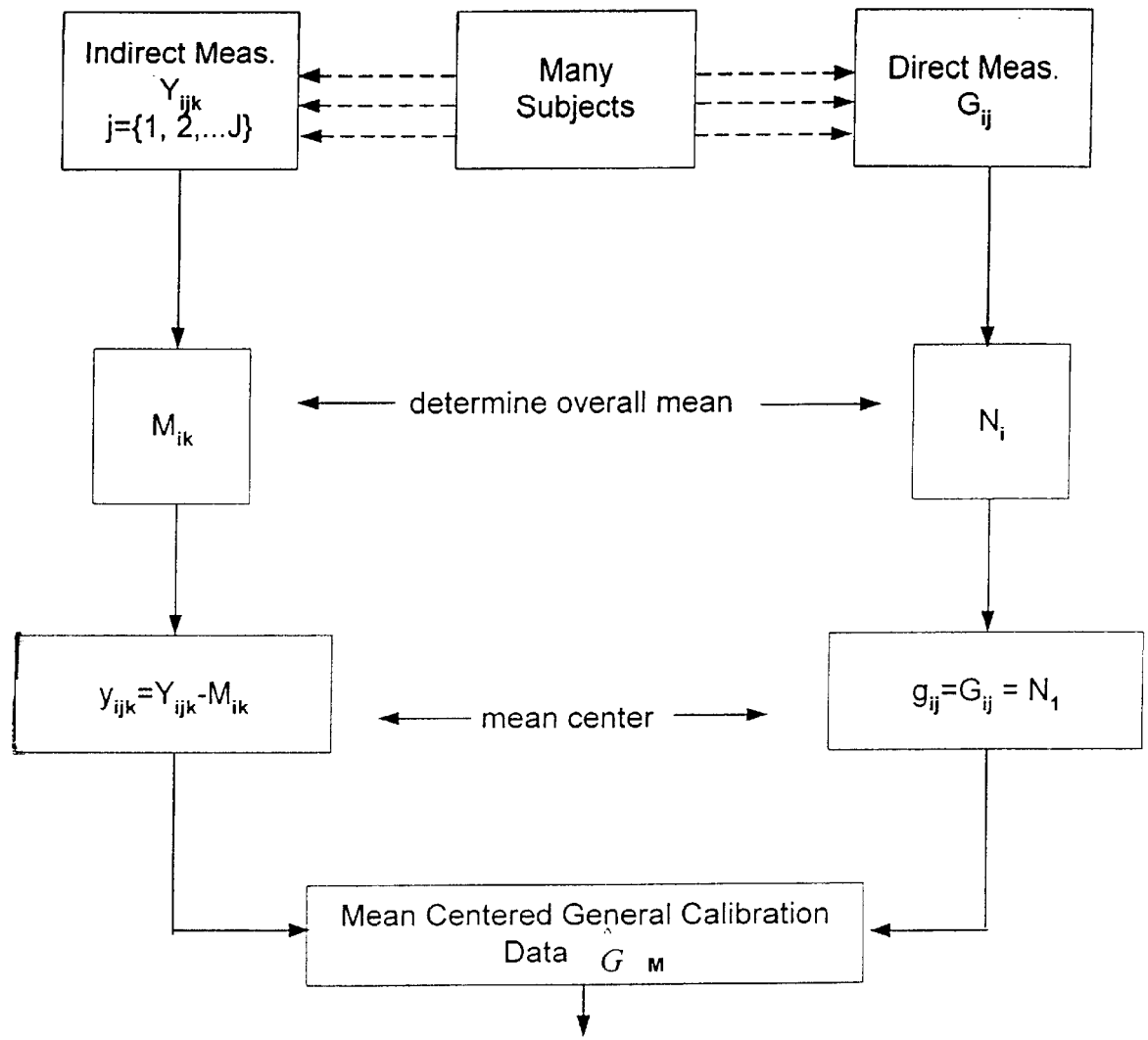
FIG. 2 is a flow chart representing the processing steps associated with generating generic calibration data through meancentering.

A preferred method to generate generic calibration data is referred to as meancentering and is depicted in the flow chart of FIG. 2. Here, let $Y_{ijk}$ be the spectral measurement (e.g., log(intensity)) of the $k^{th}$ wavelength within the $j^{th}$ spectrum from the $i^{th}$ subject. Subject-specific effects are removed as follows. First, form the mean spectrum for each subject. The mean spectrum at the $k^{th}$ wavelength for the $i^{th}$ subject is:

$$M_{ik} = \frac{1}{J_i} \sum_{j=1}^{J_i} Y_{ijk}$$

where $J_i$ is the number of spectra from the $i^{th}$ subject. The appropriate mean spectrum is then removed from each observed spectrum: $y_{ijk} = Y_{ijk} - M_{ik}$. This process may be referred to as meancentering the spectra by subject.

Associated with each spectrum, we also have a direct measurement of reference blood-glucose concentration, $G_{ij}$. The glucose concentrations are also meancentered by subject, resulting in $g_{ij}=G_{ij}-N_i$, where $N_i$ is the mean glucose concentration for the $i^{th}$ subject and defined as:

$$N_i = \frac{1}{J_i}\sum_{j=1}^{J_i} G_{ij}$$

The meancentered glucose values may be scaled by a subject-specific factor (k) that is equal to the relative magnitude of the spectral effect of 1 mg/dL of in vivo blood-glucose for that subject. This scaling serves to normalize glucose signals across subjects that could be different across subject (e.g., due to pathlength differences) to a standard in vivo glucose signal. The particular example of meancentered processing is cited to illustrate a specific processing embodiment of the invention. It is recognized that the use of this invention may involve generation of generic calibration date through multiple processing means. Subject-specific spectroscopic variances can be reduced by subtracting (in absorbance units, or performing a similar operation in any other data space) some linear combination of each subject's reference spectra and reference analyte values. At this point, the meancentered spectra and meancentered (and possibly scaled) glucose concentrations are used in the multivariate calibration model development.

Once the generic calibration data has been created, such data are then utilized in forming a tailored prediction process for a particular subject for use in future predictions of the biological attribute. This can be accomplished in several ways such as use of a direct-tailoring technique or alternatively a composite technique. Common to both methods is a calibration model. A representation of a linear multivariate calibration model (a specific type of calibration model) is $\hat{G}=b_0+b_1 \cdot y_1+b_2 \cdot y_2+ \ldots +b_q \cdot y_q$, where the $b_k$'s are model parameters. Development of G from the meancentered indirect data $y_{ijk}$ or other generic calibration data and the direct data $g_{ij}$ is a routine matter for one skilled in chemometrics, as taught by H. Martens et al., *Multivariate Calibration*, (1989), John Wiley, Chichester.

Note that the use of generic calibration data for developing the generic model in this embodiment is believed important for preserving sufficient sensitivity to detect outlier (or anomalous) spectra during prediction. Without the meancentering operation of the invention on the spectra, Mahalanobis-distance and other outlier detection metrics are likely to be based heavily on ancillary inter-subject effects and, therefore, not be sufficiently responsive to unusual intra-subject effects.

Once the generic model is in hand, it must be tailored (or adapted) for a specific subject. Two direct tailoring versions of this procedure are described for the present embodiment. In the first version it is assumed that the scale factor, k, pertaining to the relative magnitude of the spectral effect of 1 mg/dL of in vivo blood-glucose is known with adequate precision. In the second version it is assumed that this scale factor is unknown and must be estimated.

Version 1 (k known)

1. Make one (or several) spectral measurement of the target subject's tissue (perhaps varying the spatial position when multiple measurements; are obtained at about the same time). Denote the resultant spectrum (or average spectrum when multiple spectra are obtained) by $Y_{ref}$, where $Y_{ref}=\{y_{r1}, y_{r2}, \ldots, y_{rq}\}$. The idea is to obtain very precise spectral measurements for the adaptation process.
2. As close as possible in time with respect to the collection of the spectrum (spectra), an accurate reference measurement of in vivo glucose, $G_{ref}$, is obtained from the subject (e.g., blood draw).
3. Use the generic model in conjunction with $Y_{ref}$ to obtain a raw prediction of glucose, $P_0$, that will be used as the basis to adapt the generic model to the subject. Once steps 1–3 have been completed, non-invasive measurements of glucose can be determined in the future as follows.
4. Obtain a new spectral measurement of the subject's tissue, $$Y_{new}=\{y_{n1}, y_{n2}, \ldots, y_{nq}\}.$$

5. Apply the generic model to $Y_{new}$ to obtain an unadapted prediction, $P_{new}$.

The prediction of glucose (adapted to that subject) is $$\hat{G}_{new} = \frac{P_{new} - P_0}{k} + G_{ref}$$

Version 2 (k unknown)

In this format, steps 1–3 (from version 1) are performed at least twice (once when the target subject is experiencing a relatively low in vivo glucose level, the other when the target subject is experiencing a relatively high in vivo glucose level). At the relatively low glucose level, we obtain:

$$Y_{new}^{lo}=\{y_{n1}^{lo}, y_{n2}^{lo}, y_{n3}^{lo}, \ldots\}$$

At the relatively high glucose level, we obtain:

$$Y_{new}^{hi}=\{y_{n1}^{hi}, y_{n2}^{hi}, y_{n3}^{hi}, \ldots\}$$

As in version 1, apply the generic model to $Y_{new}$ to obtain an uncorrected prediction, $P_{new}$. The prediction of glucose (adapted to that subject) is:

$$\hat{G}_{new} = \frac{P_{new} - P_0^{lo}}{\hat{k}} + G_{ref}^{lo}, \text{ where } \hat{k} = \frac{P_0^{hi} - P_0^{lo}}{G_{ref}^{hi} - G_{ref}^{lo}}$$

Note that it is straightforward (and perhaps desirable) to modify this technique to include more than one or two reference samples per target subject.

Figure 3:
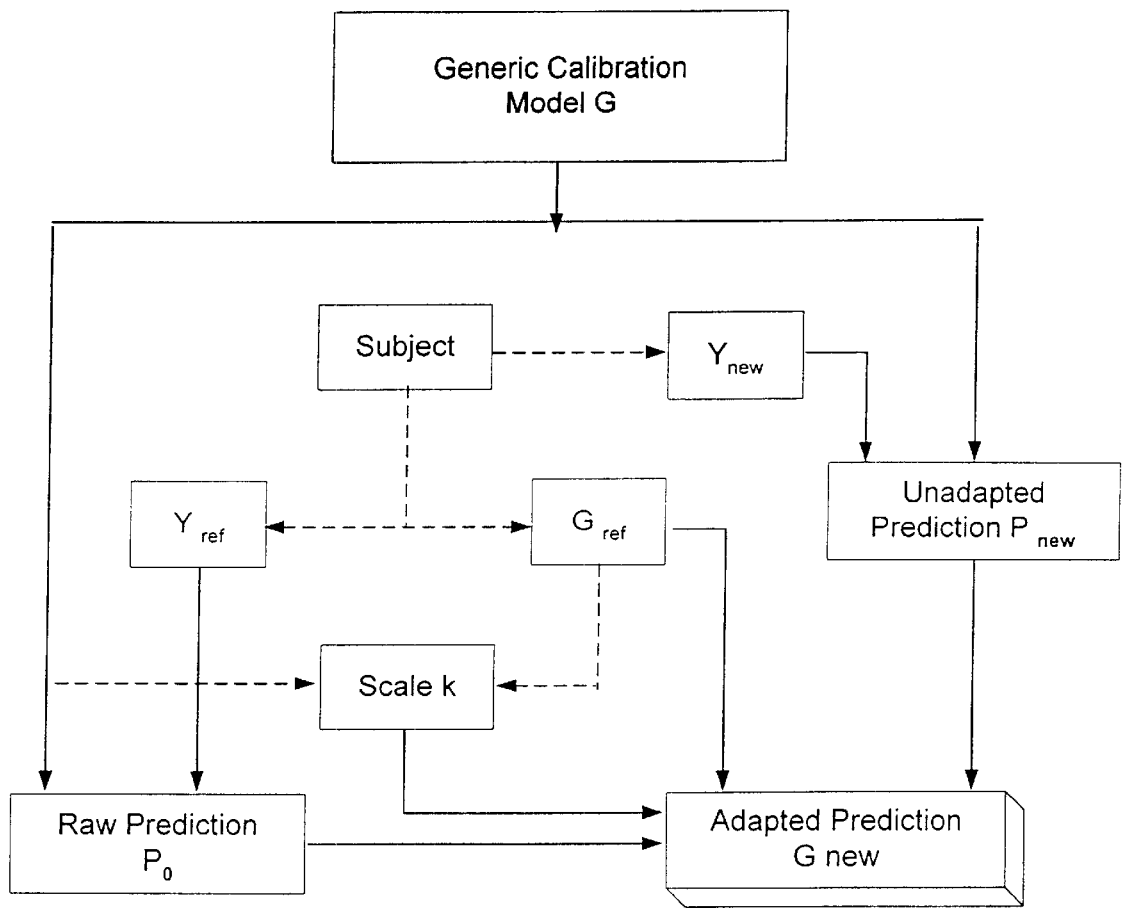
FIG. 3 is a flow chart representing the steps of the direct tailoring prediction process of the present invention.

In summary, the proposed prediction method of this first embodiment provides a solution to the difficulties associated with building a universal calibration model that needs to be appropriately responsive to subject-to-subject spectral variation as well as spectral variation within subjects over time and space. The proposed method is illustrated in the flow chart of FIG. 3 and provides a simple subject-specific adaptation to a generic model that is appropriately sensitive to the spectral variation within a subject. Development of this type of subject-specific model is a substantial improvement (with respect to efficiency) when compared to the development of subject-specific models via intensive optical sampling of each individual subject.

Figure 4:
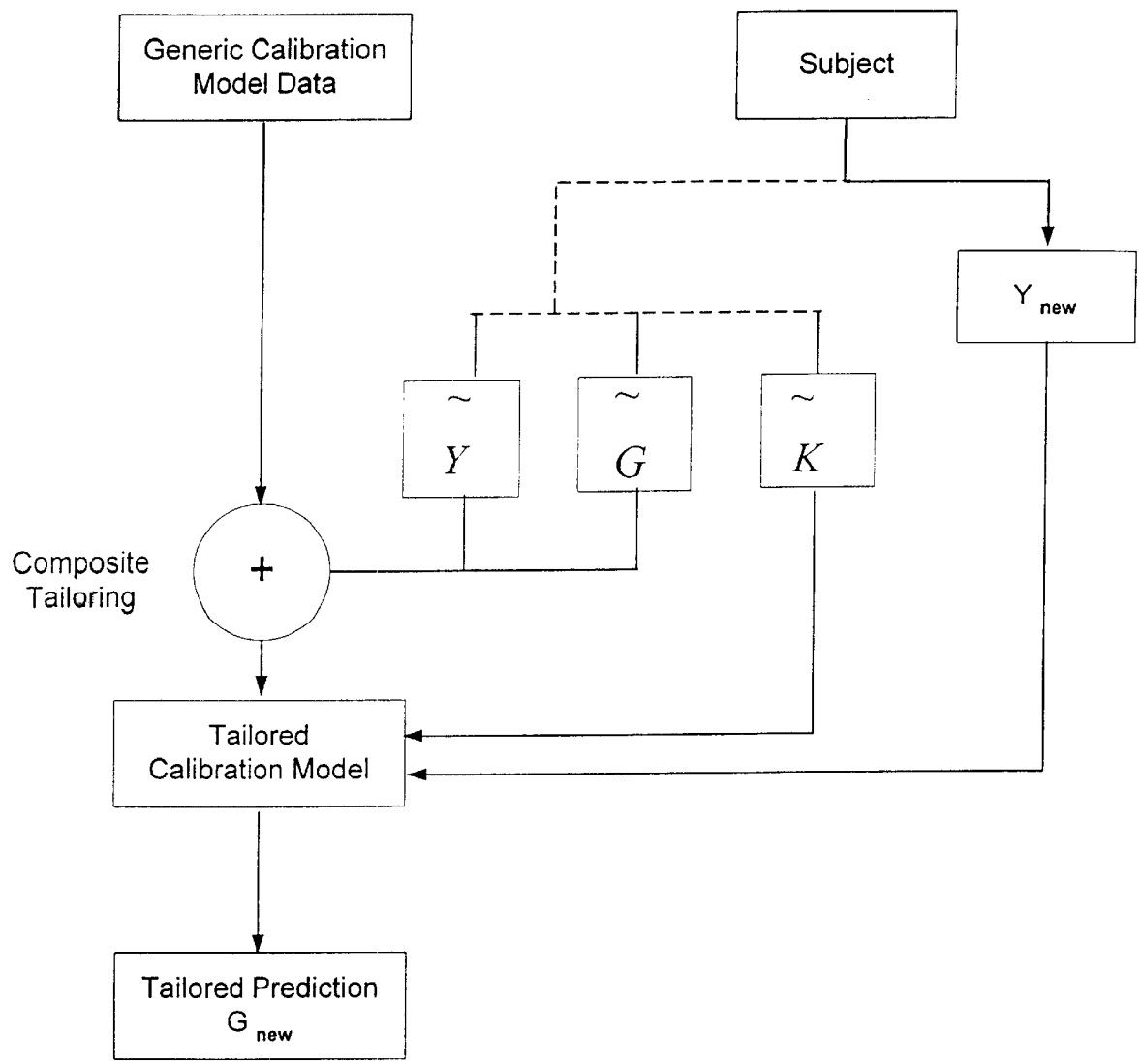
FIG. 4 is a flow chart representing the steps of the composite tailored prediction process of the current invention.

The second prediction technique of the present invention is the composite technique that is depicted in the flow chart of FIG. 4. With the composite technique, two or more reference measurements, which include both the spectra and the analyte reference values, are made on the particular subject and these data are added in a random fashion to the generic calibration data. This process is represented by the equations:

$$y_{ijk}=y_{ijk}+y_{ilk}^{ref},\ g_{ij}=g_{ij}+g_{ij}^{ref},$$

where $y_{ilk}^{ref}$ is the $k^{th}$ element of the $l^{th}$ reference spectrum for subject i, $g_{il}^{ref}$ is the $l^{th}$ glucose reference value for subject i, and a random value of l is chosen for each i, j pair The resulting composite data is then used in conjunction with a multivariate analysis technique to generate a calibration model which is subject tailored due to the addition of reference spectral measurements and reference analyte measurements prior to generating the model. The resulting subject-tailored model is then applied to other spectra from the same subject on whom the reference measurements were made. Predictions are made with the resulting calibration model by following standard chemometric practices known to one skilled in the art.

Figure 5:
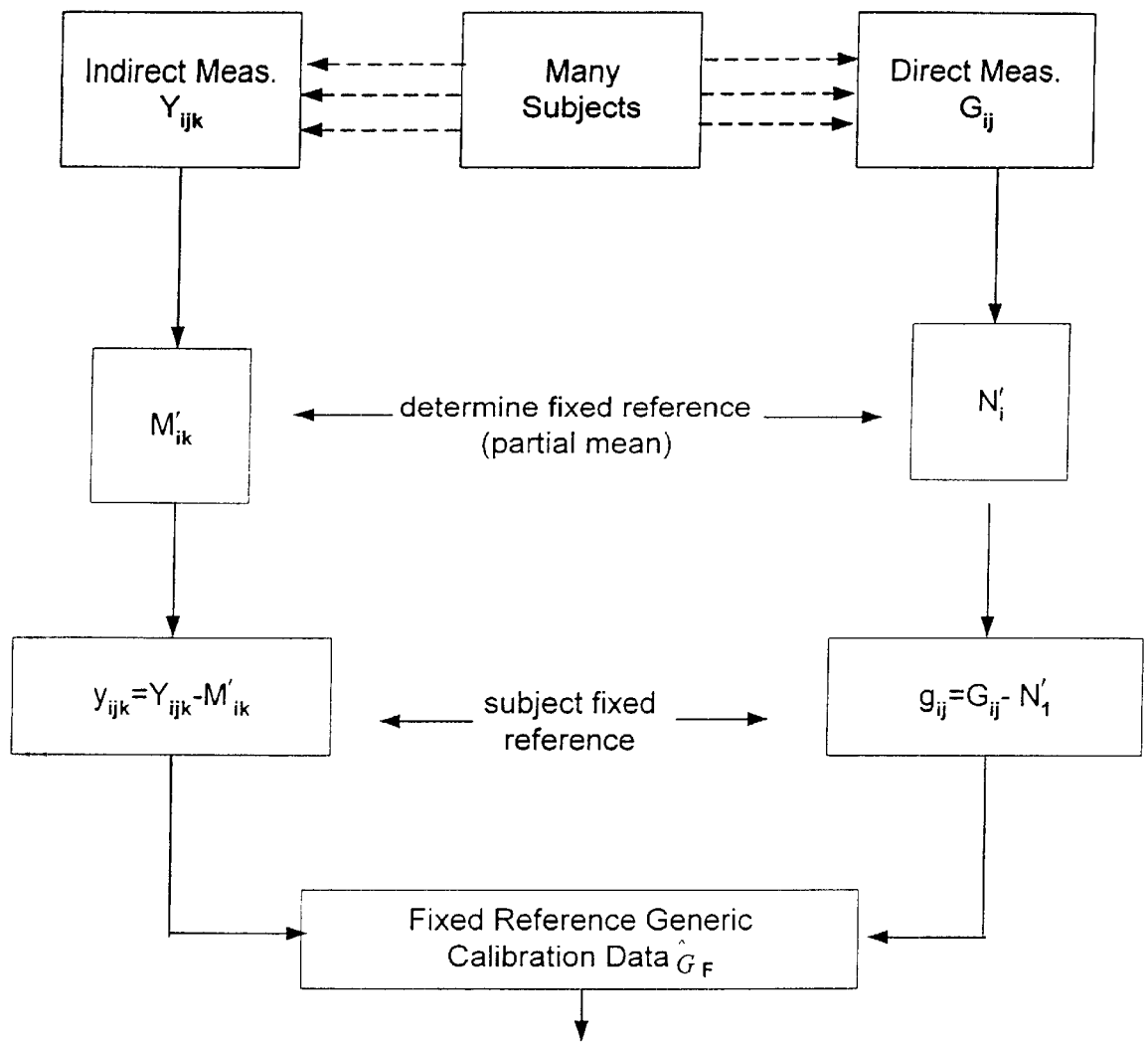
FIG. 5 is a flow chart representing the processing steps associated with generating generic calibration data through the fixed reference method.

Generic calibration data can also be created by a fixed reference technique. The fixed reference technique is depicted in the flow chart of FIG. 5. This technique can be utilized to modify the calibration data by subtracting the mean of the first S calibration spectra and reference values from a particular subject from each of the subject's reference measurements, where S is less than the total number of reference measurements made on a particular subject. This is represented by the equations:

$$M_{jk} = \frac{1}{S}\sum_{j=1}^{S} Y_{ijk},\ N_i = \frac{1}{S}\sum_{j=1}^{S} G_{ij},\ \text{where } S < J_i$$

In the alternative, a moving window reference technique may be utilized wherein you subtract the mean of the S nearest (in time) calibration spectra and reference values from each of the subject's calibration measurements, where S is less than the total number of reference measurements made on a particular subject. This method is represented by the equation:

$$M_{ijk} = \frac{1}{S}\sum_{l=J-\left(\frac{S-1}{2}\right)}^{J+\left(\frac{S-1}{2}\right)} Y_{ijk},\ N_{ij} = \frac{1}{S}\sum_{l=J-\left(\frac{S-1}{2}\right)}^{J+\left(\frac{S-1}{2}\right)} G_{ij},\ \text{where } S \text{ is odd}$$

The value of S can be chosen to fit the constraints of the particular application, neglecting effects due to random noise and reference error.

Figure 6:
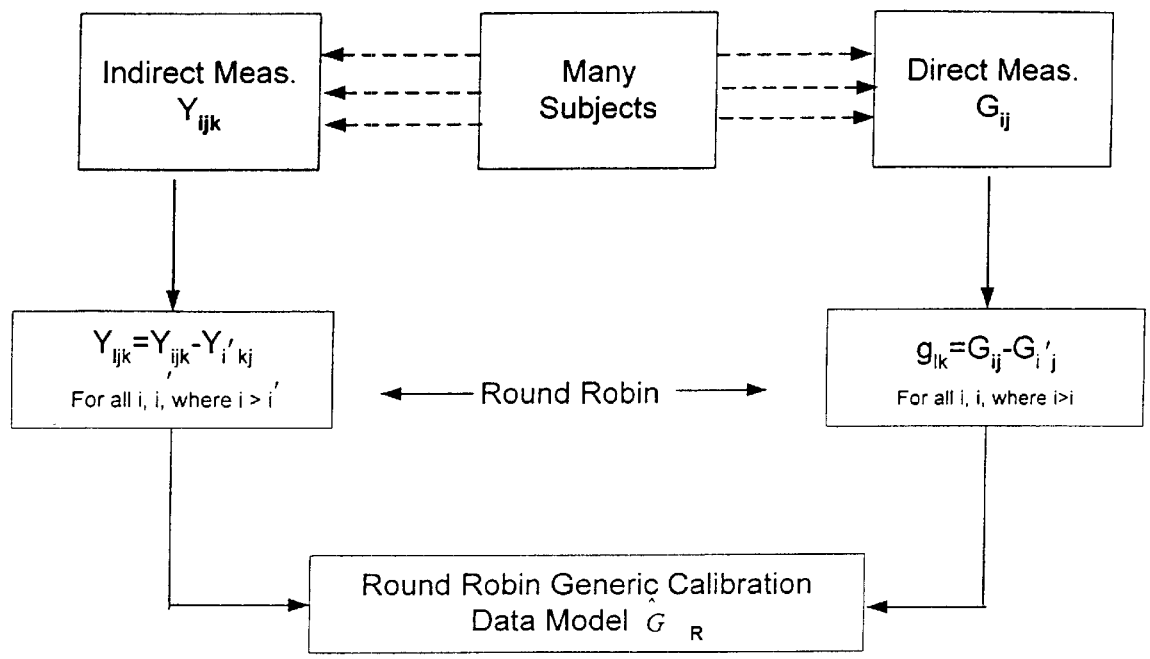
FIG. 6 is a flow chart representing the processing steps associated with generating generic calibration data through the round robin method.

Alternatively, the generic calibration data may be generated in a round-robin reference manner wherein you subtract each of the patient's reference data from every other reference measurement made on that subject in a round-robin fashion. The round-robin method is depicted in the flow chart of FIG. 6. This method is represented by the equations:

$$\left. \begin{array}{l} y_{ilk} = Y_{ij_lk} - Y_{ij'_lk} \\ g_{il} = g_{ij_l} - g_{ij'_l} \end{array} \right\} \quad \text{For all } j,\ j' \text{ where } j'_l > j_l$$

Figure 7:
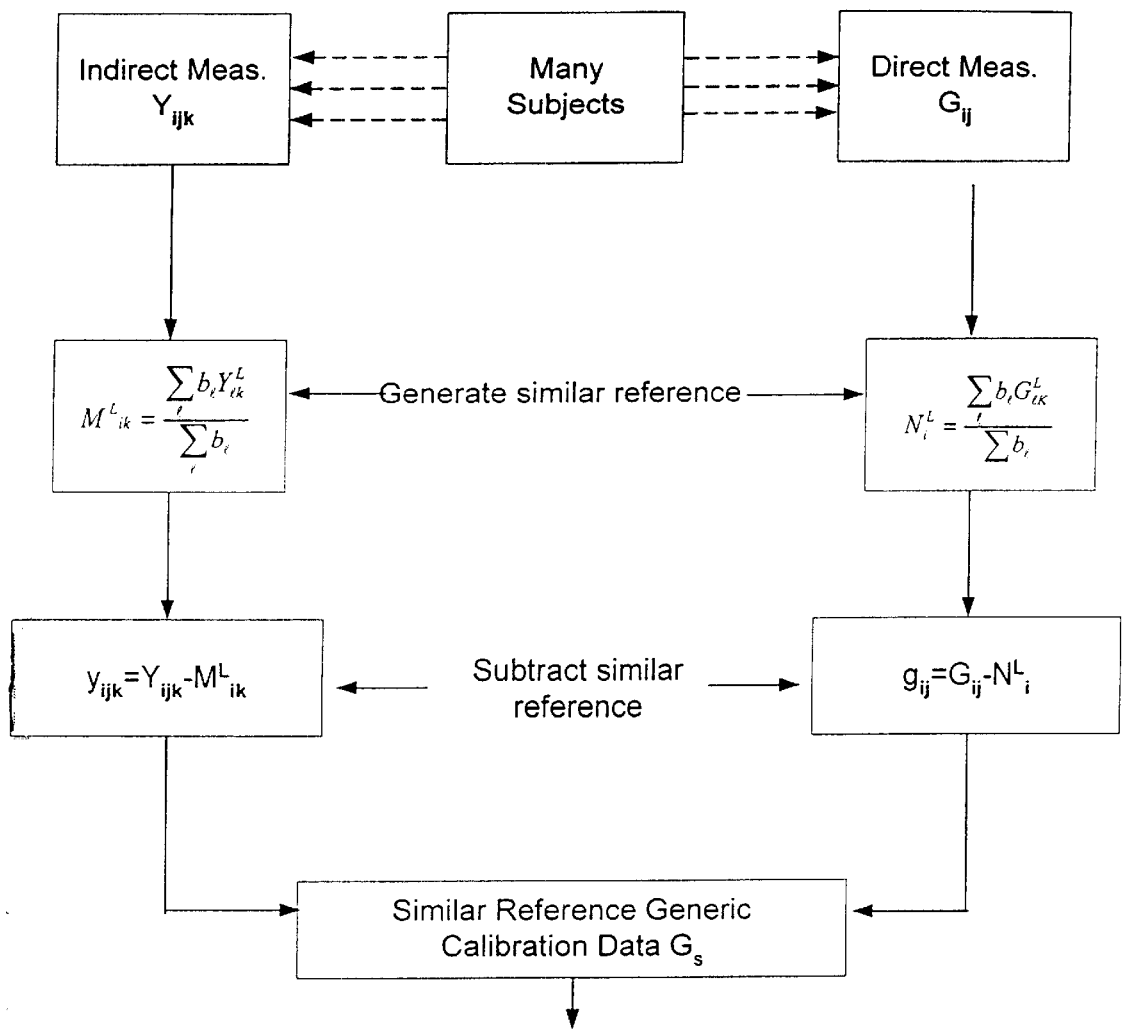
FIG. 7 is a flow chart representing the steps of the composite tailored prediction process of the current invention.

A final method used for generating generic calibration data is particularly useful where a large spectral library, including spectra and reference values from multiple people exists. The library data are modified to reduce or eliminate subject-specific spectral attributes by subtracting some linear combination of spectral library data in order to minimize cross-subject spectral features. The methods of this embodiment are depicted in the flow chart of FIG. 7. Thus in modifying the spectral library data, to create generic calibration data, a given subject's spectra are modified through the use of a similar patient spectra. Similar patient spectra are those spectra that when subtracted from a specific subject results in a spectral difference that is less than the average difference across all subjects. The similar spectrum can be from another subject or can be formed by combining several subjects to create a similar spectrum.

In an additional embodiment, patient spectra are created through simulation in a manner that minimizes subject-specific spectral attributes. This methodology requires accurate simulations of patient spectra, which would include high accurate modeling of the optical system, the sampler-tissue interface, and the tissue optical properties which all contribute to such spectral variation. Such simulated data can be, generated and removed from measured calibrated data to reduce patient-specific characteristics. The modified calibration model data can then be utilized in conjunction with data from a specific patient to tailor the model for use in predicting biological attributes of that patient with the above methods.

Figure 8:
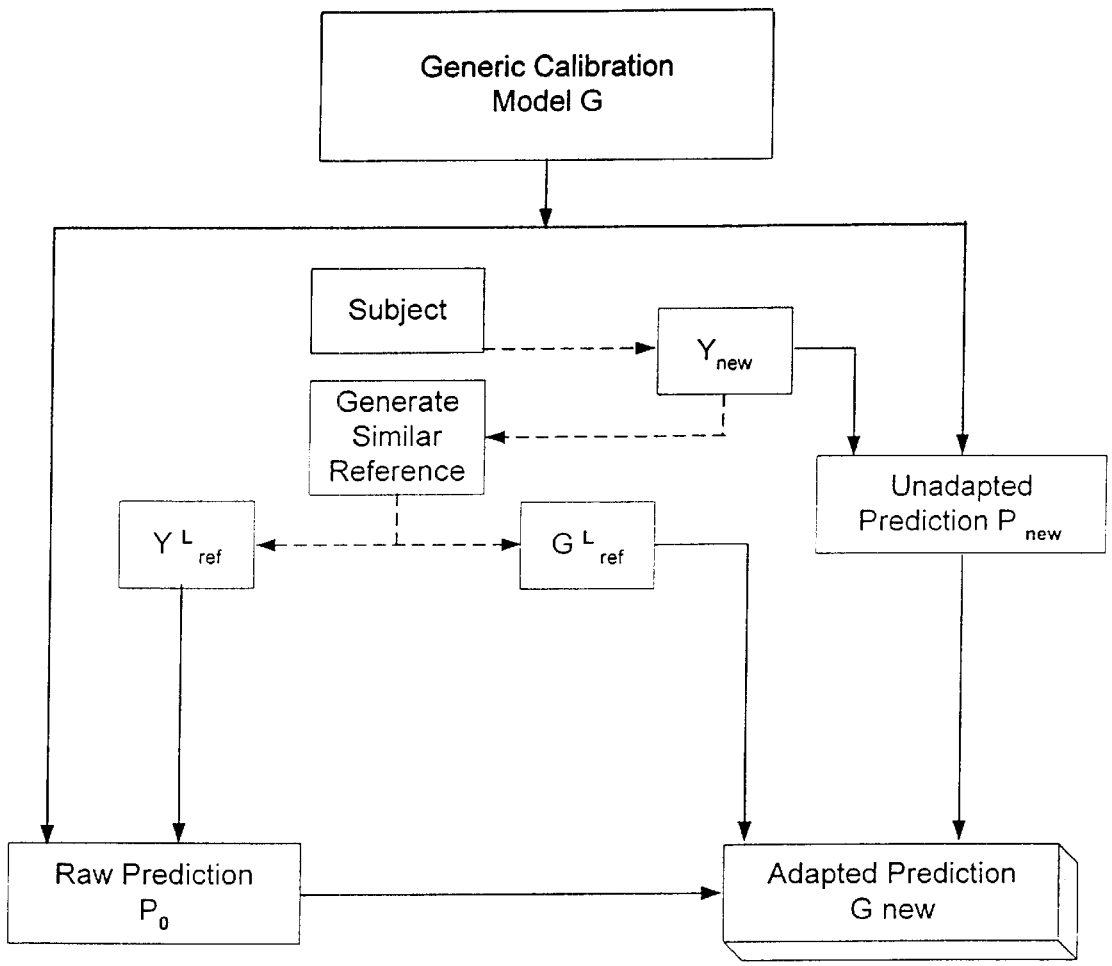
FIG. 8 is a flow chart representing the steps of the matched spectrum method in conjunction with the direct-tailored prediction process of the current invention.
Figure 9:
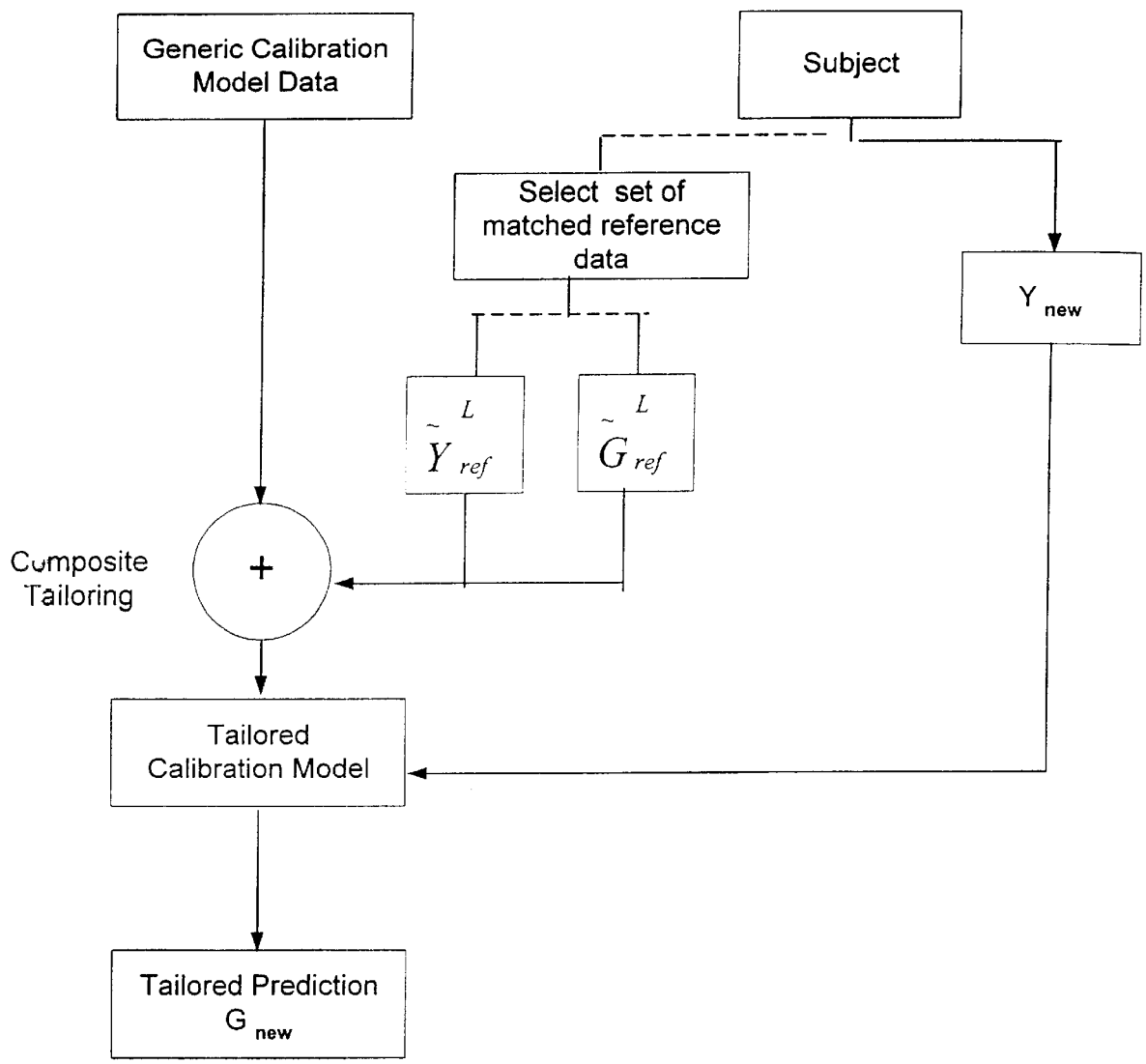
FIG. 9 is a flow chart representing the steps of the matched spectrum method in conjunction with the composite tailored production process of the current invention.

Once the generic calibration data has been created, such data is then utilized in forming a tailored prediction process for a particular subject for use in future predictions of the biological attribute. This can be accomplished in several ways, such as use of the direct-tailored technique, or alternatively, the composite technique previously described With either the direct-tailored prediction method or the composite tailored prediction method as previously described, the reference spectra can be replaced by a matched spectra. The flow charts of FIGS. 8 and 9 depict matched spectra methods with bidirects tailored prediction and composite tailored prediction, respectively. With this method, a never-before-seen subject is then tested and at least one target spectrum or set of spectral data is acquired. However, no analyte or direct measurement is required from the patient. Rather, the spectral data from the never-before-seen patient is compared with spectral data which has corresponding biological attribute reference values in a spectral library to identify the best reference spectrum or spectra that corresponds to the target spectrum of the never-before-seen patient. This reference spectrum can be compared with the target spectrum to determine the level of match. Thus, the subject tailoring with this method is accomplished without an actual reference analyte value. This method relies on a large spectral library to facilitate the appropriate matching between a target spectrum and a single spectral library entry or several library entries.

In the direct-tailored prediction method the matched spectrum and corresponding reference analyte values are used instead of actual reference spectra and analyte values from the subject to be predicted upon. The following equations define the substitution and prediction steps:

$$\hat{G}_{new}=P_{new}-P_0^{SIM}+G_{ref}^{SIM}\ \text{where}$$

$P_{new}$ is the raw prediction of the new spectrum $Y_{new}$ using the generic model, $P_0^{SIM}$ is the raw prediction of the similar spectrum $Y^{SIM}$ identified in the spectral library, $G_{ref}^{SIM}$ is the referenced valve associated with the similar spectrum identified in the spectral library One requirement of this methodology is the ability to find an appropriate match within the spectral library. If no single subject is an appropriate match, a matched spectrum can be created by combining spectra from other patients. In practice the matched spectrum, a combination of spectra and inference values from subject in the spectral library, is created through a weighted linear combination of absorbance spectra. The various coefficients applied to the individual library spectra can be adjusted such that the best possible match is obtained. The matched spectrum created through other subject combinations is created by the following equations:

$$Y_K^{SIM} = \frac{\sum_{J=1}^{S} c_j \, y_{JK}^{SIM}}{\sum_{j=1}^{S} c_j} \qquad G_{ref}^{SIM} = \frac{\sum_{j=1}^{S} c_j \, G_j^{SIM}}{\sum_{j=1}^{S} c_j}$$

where $y_{JK}^{SIM}$ is the $K^{th}$ element of the $J^{th}$ spectrum selected from the spectral library, $G_j$ is the corresponding reference value, and the coefficients, c, are chosen to optimize the spectral similarity with $Y_{new}$.

The resulting matched spectrum and reference value is used in a manner consistent with a matched spectrum obtained from a single patient.

In using the composite tailored prediction process generic calibration data is combined with one or more reference spectra and reference values to create a data set that is subsequently used for generation of a calibration model. The reference spectra used for the composite tailored process can be replaced by matched spectra. In practice a fixed number of best-matched spectra from the subject library can be used as reference spectra. In an alternative method any spectra which meet a predetermined level of matching could be used as reference spectra. In practice, the level of match has been determined by first calculating the difference between the target spectrum and the possible matched spectrum. The resulting difference spectrum is then used in conjunction with the calibration model to determine such parameters as the Mahalanobis distance and spectral residual metrics.

Once appropriate matched spectra are determined these spectra are used in a manner consistent with the composite tailored prediction method using reference spectra from the actual subject to be predicted upon.

In addition to the above benefits, application of the methods disclosed herein, such as monitoring blood/glucose levels non-invasively in the home where a single instrument unit (e.g., spectrometer) is paired with a single subject, provides some substantial benefits with respect to calibration transfer and maintenance. Calibration transfer refers to the process of migrating a master calibration model to a specific unit. Due to manufacturing variation across units, each unit will differ in subtle ways such that the same object will appear slightly different across units (e.g., resulting in slightly different spectra in the case of spectroscopy). Calibration maintenance refers to the process of maintaining a functional model across different instrument states (e.g., induced by changing a discrete component). The generic subject model (which is based on data that has within subject variation removed) is in fact a generic instrument/subject model. That is, the specific effect of the instrument has also been removed through the process used to modify the data set. Preferably, a generic instrument/subject model is developed by combining data across units and subjects within a unit. In either case (using a single unit or multiple units for developing a generic model), one can see that the series of measurements that are taken to adapt to the subject simultaneously and implicitly provide adaptation to the specific instrument and current instrument state. Thus, this single generic model is adaptable to an arbitrary subject being measured on an arbitrary unit from an entire production run of instruments. Furthermore, this method will facilitate the detection of anomalous conditions with respect to the subject and instrument during prediction.

EXAMPLES OF METHOD

A number of clinical studies have recently been performed to assess the performance of some of the subject tailored prediction methods disclosed in this application. In one such study, generic calibration data were obtained from 18 diabetic subjects who were repeatedly measured over a span of 7 weeks. The intent of observing the subjects for such a long period of time was to develop calibration data that spanned significant levels of natural intra-subject physiological variation (including but not limited to glucose variation) and sampling variation. In addition, the study protocol involved the deliberate perturbation of the spectrometer and its local environment to induce instrumental/environmental effects into the generic calibration data. These perturbations were carefully selected to span the expected long-term operating conditions of the instrument. Activities, such as these, are extremely important for developing generic calibration data that will facilitate valid predictions into the future.

Spectral and reference data were acquired twice per week from most subjects. A few subjects were unable to keep all of their appointments to provide spectral and reference data. During each appointment, 5 separate spectral measurements at different spatial positions on the underside of the forearm were acquired over a 15-minute period using reflectance sampling from 4200–7200 wavenumbers (390 discrete wavelengths were involved). In addition, two capillary glucose reference measurements were obtained via blood draws from each subject during each data acquisition period. The blood draws were performed immediately before and after the acquisition of the spectral data. Time-based interpolation was used to assign an appropriate capillary glucose reference value to each spectrum. A total of 1161 spectra (some acquired spectra were deemed outliers and were discarded) and associated reference glucose values comprise the calibration data.

Figure 10:
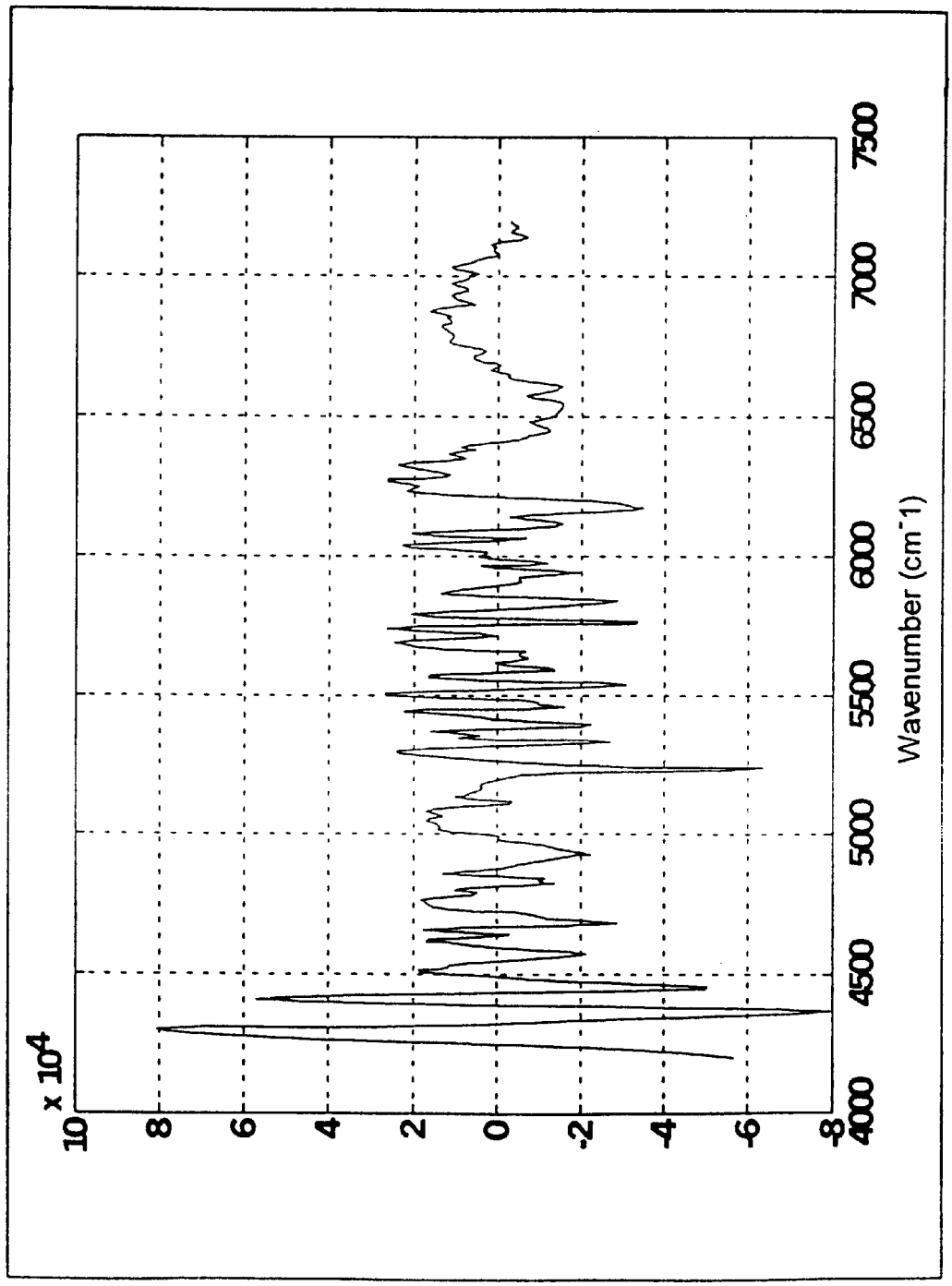
FIG. 10 displays the spectrum of generic model coefficients.

The spectral and capillary glucose reference data were mean-centered by subject to form the generic calibration data. A generic calibration model was fit to the calibration data using principal components regression without an intercept. Due to the nature of the generic calibration data (the mean-centered spectra and reference values have mean zero), the intercept is not needed. In terms of the spectral data this model is of the form, $\hat{G}=b_1 \cdot y_1 + b_2 \cdot y_2 + \ldots + b_q \cdot y_q$. The model coefficients, $(b_j, b_1, \ldots, b_q)$, are shown in FIG. 10. This model is clearly sensitive to glucose since glucose has absorption bands at 4300 and 4400.

In order to test the efficacy of the subject tailored prediction methods, the generic model was tailored (via direct tailoring) to two additional diabetic subjects who are distinct from the 18 subjects whose data were used to develop the generic calibration data/model. The period of observation for these two additional subjects spanned more than six months, beginning with the initial measurements of the original 18 subjects. Thus, the two additional subjects were observed for more than four months following the acquisition of the generic calibration data. As in the case of acquiring the calibration data, 5 separate spectral measurements at different spatial positions on the underside of the forearm were acquired over a 15-minute period during each data acquisition period. In addition, capillary glucose reference measurements were acquired from each of the two subjects during each data acquisition period according to the protocol described earlier.

Figure 11:
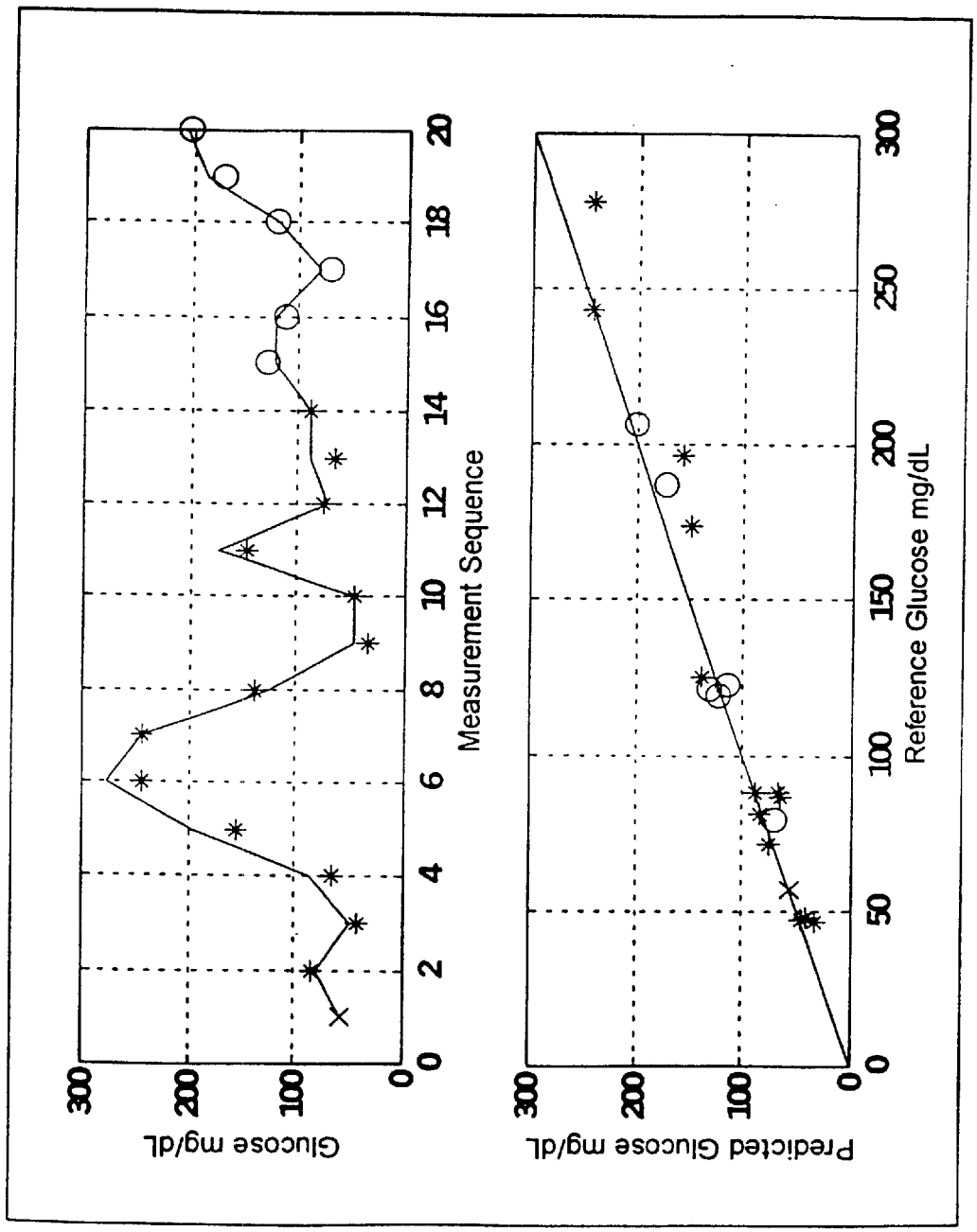
FIG. 11 graphically depicts the ability of the present invention to predict glucose sing mean centering with direct tailoring for Subject 1.
Figure 12:
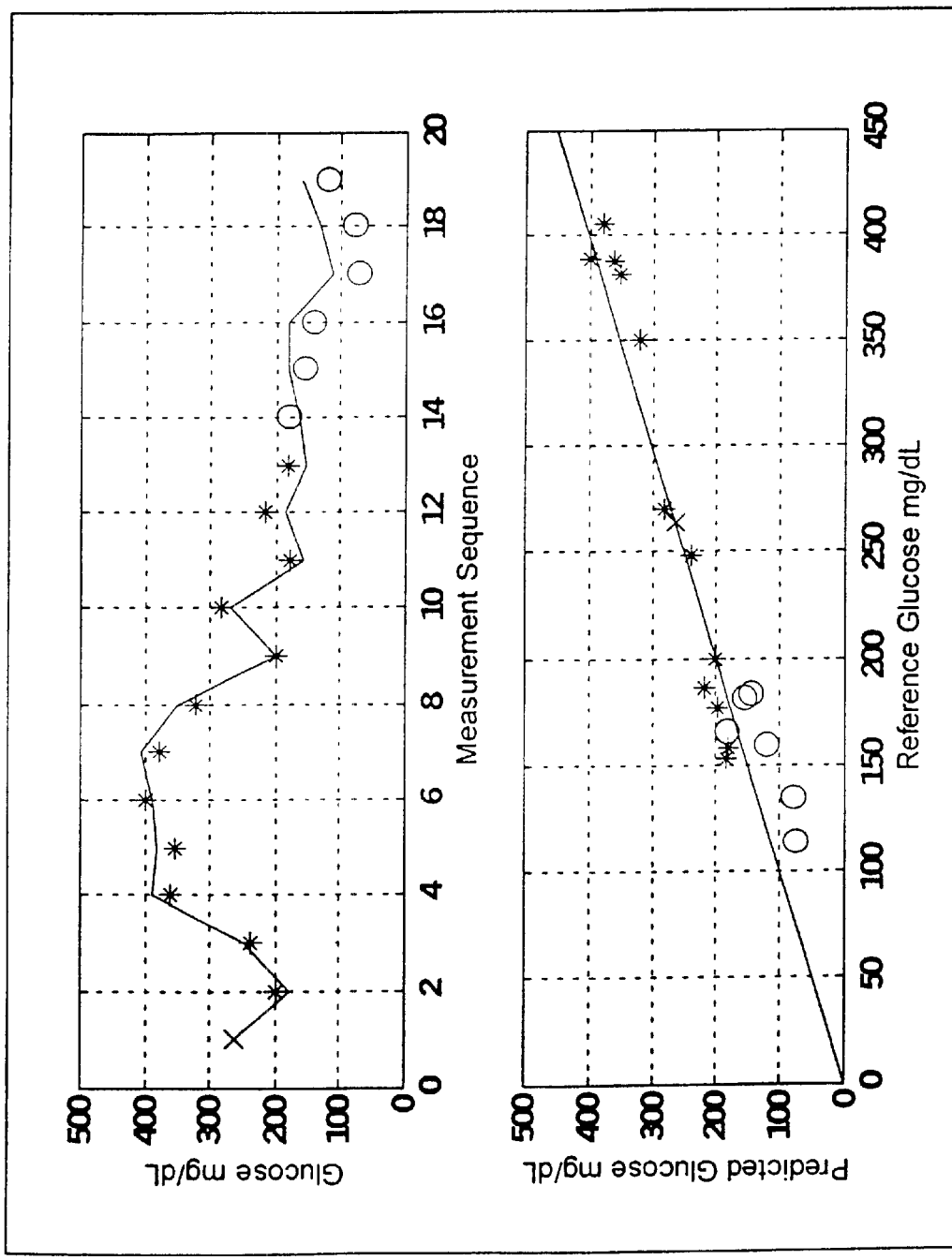
FIG. 12 graphically depicts the ability of the present invention to predict glucose using mean centering with direct tailoring for Subject 2.

During the first 7 weeks of observation and coinciding with the measurements of the original 18 subjects, the two additional subjects were observed twice per week (with one exception). The additional measurements were made were roughly 2 and 4 months beyond the initial 7-week period. The spectra and reference values obtained during the first data acquisition period were used to tailor the generic model to each subject. These tailored models were used to predict the glucose levels associated with subsequently obtained spectra. FIGS. 11 and 12 compare these predictions (averaged within a data acquisition period) with the reference measurements (also averaged within a data acquisition period) for each subject. The bottom half of each figure allows for a direct comparison of predicted glucose with the reference glucose. The top half of each figure provides a visualization of prediction performance versus time. The following conventions are used in both figures. The solid lines connect the reference glucose values over the entire measurement period. The 'x' symbols denote the predictions during the tailoring period (by definition the average prediction is identical to the average reference in this case). The '*' symbols denote predictions during the remainder of the initial 7-week period. Note that these predictions are truly prospective with respect to the unique spectral changes induced by each subject following the tailoring period. The 'o' symbols denote predictions made after the initial 7-week period. These predictions are truly prospective with respect to the unique spectral changes induced by each subject and the instrument/environment following the tailoring period. From these figures it is clear than clinically useful predictions of blood-glucose can be made using the proposed method.

It is interesting to note that there is no apparent degradation in prediction performance with respect to the first subject over the 6-month period of observation following tailoring (see FIG. 11). In contrast with respect to the second subject (see FIG. 12), prediction performance worsened over time. In this case, the tailored model consistently underpredicted glucose (by about 40 mg/dL) over the last several data acquisition periods (perhaps due to some unmodeled physiological effect). One way to remedy these systematic prediction errors would be to re-tailor (or re-adapt) the generic model to a subject on a regular basis. If needed, re-tailoring on a weekly basis would seem to be only a minor inconvenience for users of this technology.

Figure 13:
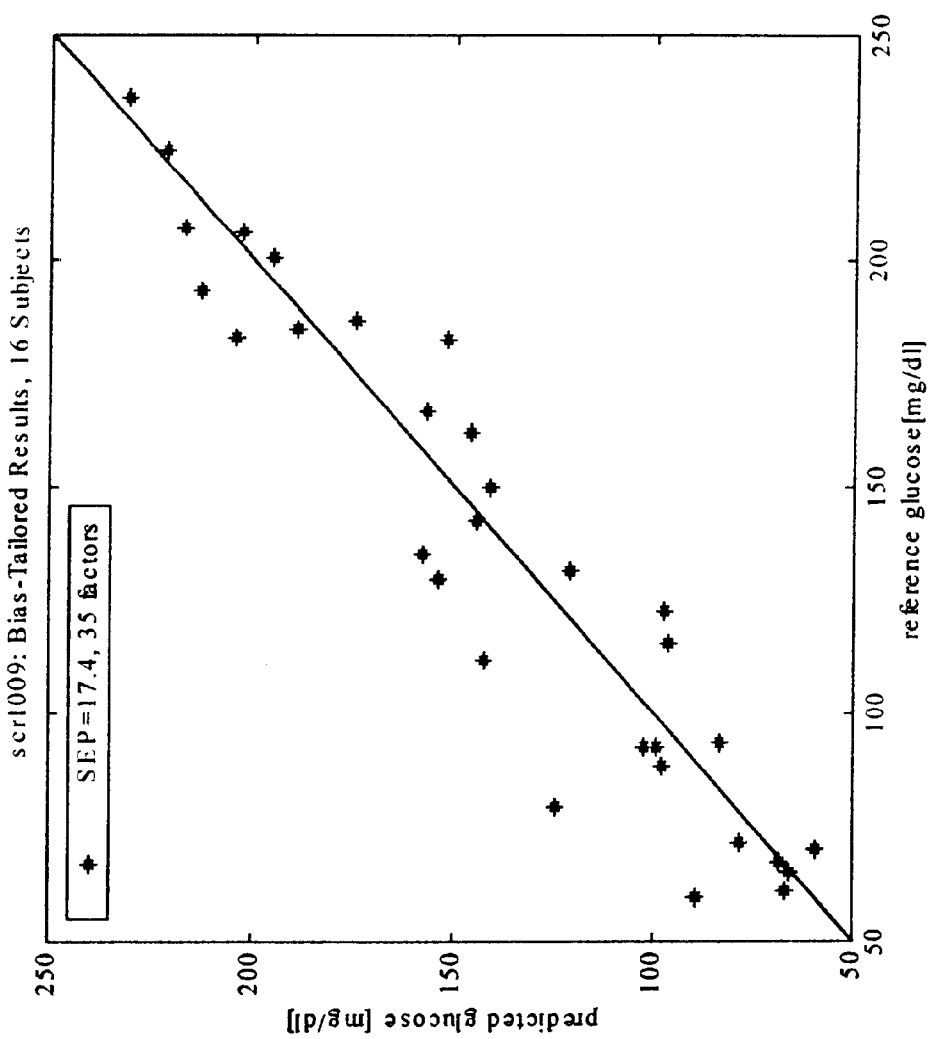
FIG. 13 graphically depicts the ability of the present invention to predict glucose with the direct tailored prediction process.
Figure 14:
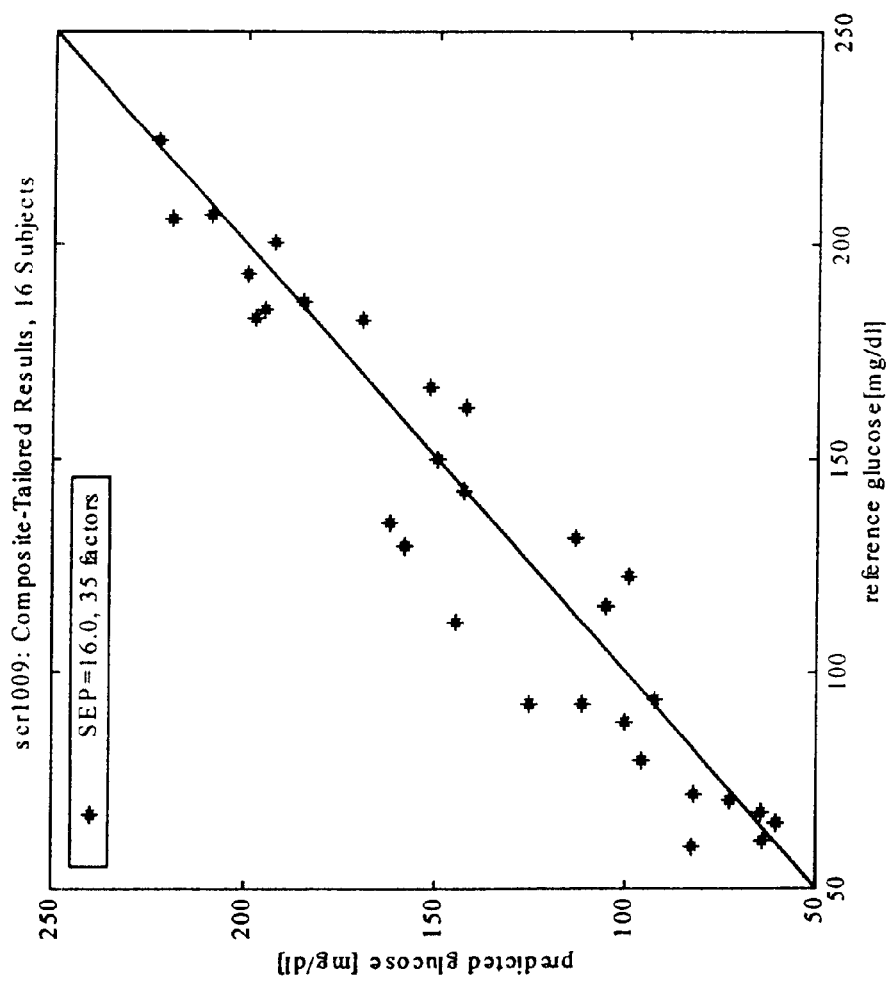
FIG. 14 graphically depicts the ability of the present invention to predict glucose with the composite tailored prediction process.

Additional tests have also been performed that enabled the subject tailored prediction methods to be tested. The test data used spectral measurements obtained from subjects over a total span of 16 weeks. The protocol for the study required that each subject have spectral measurements taken on 2 or 3 separate days per week for 8 weeks, spanning the 16-week study duration. Each time a subject came in for a study "sitting," 4 separate spectral measurements at different spatial positions on the underside of the forearm were acquired over a 15-minute period, as well as two capillary glucose reference measurements, which bounded the spectral collection. A total of 1248 spectra (reflectance sampling from 4200–7200 wavenumbers [390 discrete wavelengths]) and associated reference glucose values were used to develop the calibration data. The resulting data set was processed through the mean centering method and generic calibration data were obtained. To adequately test the true prediction capabilities of the methods, the subject to be evaluated was excluded from the data used to develop the generic calibration data. The exclusion of one patient from the calibration data with subsequent evaluation of their performance is commonly referred to as patient-out cross-validation. The cross-validated generic calibration data was adapted for each of the 16 diabetic subjects (4 subjects were not present for the entire study) and resulted in predictions the final two days of that subject's data. Adaptation to each subject was performed using data from 5 separate sittings of the subject, 4 sittings were from the first two weeks of data collection and the fifth sitting was from a day that was two days prior to the first validation day. The second validation day occurred two days after the first. FIGS. 13 and 14 provide the prospective (in time) prediction results associated with the subjects. The figures show the predicted glucose values for the two validation days relative to the corresponding glucose reference values obtained by capillary draw for all 16 subjects measured. FIG. 13 shows the results using the direct-tailored method discussed in the body of this disclosure. FIG. 14 shows the results using the composite-tailored method, also discussed earlier in this disclosure. From these figures it is clear than clinically useful predictions of blood-glucose can be made using the proposed method.

The particular examples discussed above are cited merely to illustrate particular embodiments of this invention. It is contemplated that the use of, the invention may involve methods for multivariate calibration and prediction and their application to the non-invasive or non-destructive spectroscopic measurement of selected variables in an environment. Although blood glucose (the variable) and people (the environment) are the focus of this disclosure, calibration of other variables such as blood alcohol levels, and other subjects, such as scans of a physical scene from which information about the scene is determined, is contemplated. For example, an airborne scan of a site (geophysical environment) might provide information whereby multivariate analysis of spectra could determine the amount of pollutants (the variables) at the site (the environment), if the scanning device had been calibrated for pollutants. In this case, prediction of pollutant levels would be the tailored to a particular site. In another example, one might be interested in predicting the level of a certain chemical species (the variable) in a chemical reactor (the environment) using spectral methods. If the intra-reactor spectral variability were consistent across different reactors, then generic calibration data could be obtained by using reactor-specific subtrahends. Predictions could be tailored to each reactor.

In addition, while the invention is disclosed as a method of calibrating a single measurement device, it is also contemplated that the meancentered data could be obtained form a number of units that measure both the same subjects and different subjects. Lastly, the generic calibration discussed above preferably uses more than one subject because multiple subjects permit a sufficient quantity of intra-subject variation data to be obtained in a short period of time. However, for other situations where there are not multiple subjects, such as the observation of a unique chemical process, the calibration data may be obtained from the one site over an extended period of time. It is intended that the scope of the invention be defined by the claims appended hereto.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. A method for generating a prediction result for use on a specific subject to predict a biological attribute of that subject using spectroscopy as a surrogate indirect measurement for a direct measurement of said biological attribute, said method comprising the steps of:

(a) using a calibration data set that includes spectroscopic variation from multiple subjects;

(b) generating a model by applying multivariate analysis to said calibration data set; and (c) using a prediction process to predict an unknown amount of said biological attribute in a target spectroscopic measurement that utilizes said model in conjunction with at least one matched measurement, wherein said matched measurement is obtained by using a spectral library and corresponding values of said biological attributes.

2. The method of claim 1, wherein said spectral library is generated from spectral measurements of multiple persons.

3. The method of claim 1, wherein the at least one matched measurement is obtained by selecting the spectra from said spectral library which best corresponds to said target spectroscopic measurement.

4. The method of claim 3, wherein the best corresponding measurement is selected as being those spectra from the spectral library that appear similar when processed by the calibration model.

5. The method of claim 4, wherein the determination of which spectra appear similar when processed by the calibration model is determined through the calculation of Mahalanobis distance and/or spectral residual metrics.

6. The method of claim 1, wherein said prediction process comprises:

(a) making an indirect measurement, $Y_{new}$, of the specific subject;

(b) using said model with $Y_{new}$ to obtain a raw prediction, $P_{new}$, of the biological attribute.

7. The method of claim 6, further comprising:

using said model to predict the biological attribute $G_{new}$ for the subject as a function of $P_{new}$, the prediction of said matched measurements $P_0^{SIM}$, and the reference value of said biological attribute associated with said matched measurements $G_{ref}^{SIM}$.

8. The method of claim 1, further comprising creating said matched spectrum by combining spectra from the spectral library.

9. The method of claim 8, further comprising:

creating said matched spectrum through a combination of said spectra, wherein various coefficients applied to the spectra are adjusted such that a better match is obtained.

10. A method for generating a prediction result for use on a specific subject to predict a biological attribute of that subject using spectroscopy as a surrogate indirect measurement for a direct measurement of said biological attribute, said method comprising the steps of:

(a) using a modified calibration data set that has spectroscopic variation from multiple subjects;

(b) generating a calibration model through application of a multivariate algorithm that uses a composite calibration data set that is formed by combining the modified calibration data set with one or more matched measurements, wherein said matched measurements are obtained by using a spectral library and corresponding values of said biological attributes; and (c) predicting an unknown amount of said biological attribute in a target spectroscopic measurement that utilizes said calibration model.

11. The method of claim 10, further comprising:

selecting as said matched measurements all spectra of said spectral library which meet a predetermined level of matching to the said target spectroscopic measurement.

12. The method of claim 10, further comprising:

selecting a fixed number of spectra from said spectral library which best match the target spectroscopic measurement.

13. The method of claim 10, wherein said spectral library is generated from spectral measurements of multiple persons.

14. The method of claim 10, further comprising creating said matched measurements by combining spectra from said spectral library.

15. A non-invasive method for measuring a biological attribute in human tissue of a specific subject comprising the steps of:

(a) providing an apparatus for measuring infrared absorption, said apparatus including an energy source emitting infrared energy at multiple wavelengths, an input element, an output element and a spectrum analyzer;

(b) coupling said input and output elements to said human tissue;

(c) irradiating said tissue through said input element with multiple wavelengths of infrared energy with resulting absorption of at least some of said wavelengths;

(d) collecting at least a portion of the non-absorbed infrared energy with said output element followed by determining the intensities of said infrared energy; and (e) predicting the biological attribute of said specific subject utilizing a model, wherein said model uses spectroscopic variation from multiple subjects and one or more reference measurements from said specific subject, each of said reference measurements including spectroscopic and corresponding direct measurement of said biological attribute.

* * * * *

UNITED STATES PATENT AND TRADEMARK OFFICE
CERTIFICATE OF CORRECTION

| | | |
|---|---|---|
| PATENT NO. | : 6,528,809 B1 | Page 1 of 1 |
| APPLICATION NO. | : 09/672326 | |
| DATED | : March 4, 2003 | |
| INVENTOR(S) | : Edward V. Thomas and Robert K. Rowe | |

It is certified that error appears in the above-identified patent and that said Letters Patent is hereby corrected as shown below:

Before the heading "Technical Field" at column 1, line 10, of the patent, insert the following:

Government Rights
The United States Government has rights in this invention pursuant to Contract No. DE-AC04-94AL85000 between the United States Department of Energy and Lockheed Martin Corporation for the management and operation of Sandia National Laboratory and pursuant to a cooperative research arrangement between Rio Grande Medical Technologies, Inc. and Sandia Corporation.

Signed and Sealed this

Twentieth Day of February, 2007

JON W. DUDAS
*Director of the United States Patent and Trademark Office*